United States Patent [19]

Barbachyn

[11] Patent Number: 5,523,403
[45] Date of Patent: Jun. 4, 1996

[54] TROPONE-SUBSTITUTED PHENYLOXAZOLIDINONE ANTIBACTERIAL AGENTS

[75] Inventor: Michael R. Barbachyn, Kalamazoo, Mich.

[73] Assignee: The Upjohn Company, Kalamazoo, Mich.

[21] Appl. No.: 445,594

[22] Filed: May 22, 1995

Related U.S. Application Data

[63] Continuation-in-part of Ser. No. 66,356, filed as PCT/US93/09589, Oct. 14, 1993, abandoned, which is a continuation-in-part of Ser. No. 3,778, Jan. 13, 1993, abandoned, which is a continuation-in-part of Ser. No. 988,589, Dec. 8, 1992, abandoned.

[51] Int. Cl.$^6$ ............... C07D 263/24; C07D 413/12
[52] U.S. Cl. ............. 544/137; 544/58.7; 544/369; 546/209; 546/271.4; 548/232
[58] Field of Search ................. 544/137, 369; 546/209, 275; 548/232

[56] References Cited

U.S. PATENT DOCUMENTS

| | | |
|---|---|---|
| Re. 29,607 | 4/1978 | Fauran et al. |
| 4,128,654 | 12/1979 | Fugitt et al. |
| 4,250,318 | 2/1981 | Dostert et al. |
| 4,340,606 | 7/1982 | Fugitt et al. |
| 4,461,773 | 7/1984 | Gregory . |
| 4,476,136 | 10/1984 | Dostert et al. |
| 4,705,799 | 11/1987 | Gregory . |
| 4,801,600 | 1/1989 | Wang et al. |
| 4,921,869 | 5/1990 | Wang et al. |
| 4,948,801 | 8/1990 | Carlsson et al. |
| 4,977,173 | 12/1990 | Brittelli et al. |
| 5,164,510 | 11/1992 | Brickner ................. 548/232 |

FOREIGN PATENT DOCUMENTS

| | | |
|---|---|---|
| 0127902 | 12/1984 | European Pat. Off. |
| 0184170 | 6/1986 | European Pat. Off. |
| 0312000 | 4/1989 | European Pat. Off. |
| 0316594 | 5/1989 | European Pat. Off. |
| 0352781 | 1/1990 | European Pat. Off. |

OTHER PUBLICATIONS

Eustice, D. C., Feldman, P. A., Zajac, I., and Slee, A. M., "Mechanism of Action of DuP 721: Inhibition of an Early Event during Initiation of Protein Synthesis", Antimicrobial Agents and Chemotherapy, Aug. 1988, pp. 1218–1222, vol. 32.

Gregory, Walter A., Brittelli, David R., Wang, C.–L. J., Wuonola, Mark A., McRipley, Ronald J., Eustice, David C., Ebely, Virginia S., Bartholomew, P. T., Slee, Andrew M., Forbes, Martin F., "Antibacterials. Synthesis and Structure–Activity Studies of 3-Aryl-2-oxooxazolidines. 1. The B Group", J. Med. Chem., 1989, vol. 32, pp. 1673–1681.

Gregory, Walter A., Brittelli, David R., Wang, C.–L. J., Kezar, Hollis S., Carson, Randall K., Park, Chung–Ho, Croless, Peter F., Miller, Steven., J. Rajagopalan, P., Wuonola, Mark A., McRipley, Ronald J., Eberley, Virginia S., Slee, Andrew M., Forbes, Martin, "Antibacterials. Synthesis and Structure Activity Studies of 3-Aryl-2-oxooxazolidines, 2. The A Group", J. Med. Chem., 1990, vol. 33, pp. 2569–2578.

Park, Chung–Ho, Brittelli, David R., Wang C. L.–J., Marsh, Frank D., Gregory, Walter A., Wuonola, Mark A., McRipley, Ronald J. Eberly, Virginia S., Slee, Andrew M., Forbes, Martin, "Antibacterials, Synthesis and Structure–Activity Studies of 3-aryl-2-oxooxazolidines. 4. Multiply–Substituted Aryl Derivatives", J. Med. Chem., 1992, vol. 35, pp. 1156–1165.

Primary Examiner—Robert W. Ramsuer
Attorney, Agent, or Firm—Donald L. Corneglio

[57] ABSTRACT

A novel class of phenyloxazolidinone antibacterial agents which have, as their salient structural feature, an appended substituted tropone moiety, are described. Intermediates and processes for the preparation of these antibiotics are also disclosed. These compounds are useful antibacterial agents to eradicate or control susceptible organisms.

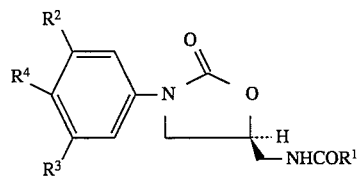

wherein $R^4$ is oxygen substituted heptatrienyl and $R^1$, $R^2$, and $R^3$ are as defined herein.

10 Claims, No Drawings

TROPONE-SUBSTITUTED PHENYLOXAZOLIDINONE ANTIBACTERIAL AGENTS

CROSS-REFERENCE TO RELATED APPLICATIONS

This application is a continuation of PCT/US93/09589, filed 14 Oct. 1993, which was a continuation-in-part of 08/066,356, filed 21 May 1993, abandoned; which was a continuation-in part of 08/003,778 filed 13 Jan. 1993, abandoned; which was a continuation-in-part of 07/988,589, filed 8 Dec. 1992, abandoned.

FIELD OF THE INVENTION

This invention relates to novel Tropone-substituted phenyloxazolidinone compounds that are useful as anti-bacterial agents.

BACKGROUND OF THE INVENTION

The oxazolidinones are a class of orally-active, synthetic antibacterial agents and there are numerous references in the art disclosing a variety of oxazolidinone derivatives. For example, there are a number of references to 3-phenyl-2-oxazolidinone compounds having one, two or three substitutions on the phenyl ring. References disclosing a single substitution to the phenyl ring include U.S. Pat. No. 4,948,801; 4,461,773; 4,340,606; 4,476,136; 4,250,318; 4,128,654, and Re 29,607. Additional references to 3-[(monosubstituted)phenyl]-2-oxazolidinones can be found in EP Publication 0 312 000, Gregory, et al., J. Med. Chem. 32:1673 (1989), Gregory, et al., J. Med. Chem. 33:2569 (1990), Park, et al., J. Med. Chem. 35:1156 (1992) and Wang, et al., Tetrahedron 45:1323 (1989). Compounds of this type also include the antibacterial DuP721.

3-[(di-,tri- or fused-ring substituted)phenyl]-2-oxazolidinones are reported in U.S. Pat. Nos. 4,977,173, 4,921,869, and 4,801,600; EP Publications 0 316 594, 0 184 170, and 0 127 902; and PCT Applications PCT/US89/03548, PCT/US90/06220, PCT/US92/08267 and U.S. application Ser. No. 07/880,492 filed May 8, 1992.

We have discovered 3-[(mono-, di- and tri-substituted)phenyl]-2-oxazolidinones which are effective as antibacterial agents. The compounds of the invention are characterized by 3-phenyl-2-oxazolidinones having a tropone or substituted tropone ring at the p-position of the phenyl ring and optional additional substitution(s) with various radicals at the m-position of the phenyl ring.

INFORMATION DISCLOSURE

The following references disclose 3-phenyl-2-oxazolidinones having a single substitution on the phenyl ring.

U.S. Pat. No. 4,948,801 discloses 3-[(aryl and heteroaryl)phenyl]-2-oxazolidinones having antibacterial activity.

U.S. Pat. No. 4,476,136 discloses 3-[(p-arylalkyl, arylalkenyl, and arylacetylenic substituted)phenyl]-5-(aminomethyl)-2-oxazolidinones which have antibacterial activity.

U.S. Pat. No. 4,461,773 discloses substituted 3-phenyl-5-(hydroxymethyl)-2-oxazolidinones which have antibacterial activity.

U.S. Pat. No. 4,340,606 discloses substituted 3-[(p-alkylsulfonyl)phenyl]- 5-(hydroxymethyl)- or (acyloxymethyl)-2-oxazolidinones having antibacterial activity in mammals.

U.S. Pat. No. 4,250,318 discloses substituted 3-phenyl-5-(hydroxymethyl)-2-oxazolidinones having antidepressive utility.

U.S. Pat. No. 4,128,654 discloses substituted 3-phenyl-5-(halomethyl)-2-oxazolidinones which are useful in controlling fungal and bacterial diseases of plants.

U.S. Pat. No. Re. 29,607 discloses substituted 3 phenyl-5-(hydroxymethyl)-2-oxazolidinones having antidepressive, tranquilizing and sedative utility.

Belgian Pat. No. 892,270 discloses the 3-[(arylalkyl, arylalkenyl or arylacetylenic substituted)phenyl]-5-(aminomethyl)-2-oxazolidinones corresponding to U.S. Pat. No. 4,476,136 listed above.

European Pat. No. Publication 0 352 781 discloses aryl and heteroaryl substituted 3-phenyl-2- oxazolidinones corresponding to U.S. Pat. No. 4,948,801 listed above.

European Pat. No. Publication 0 312 000, as reported in Derwent 89-116142/16, discloses phenylmethyl and pyridinylmethyl substituted 3-phenyl-2-oxazolidinones.

C.-H. Park, et al., J. Med. Chem. 35:1156 (1992), W. A. Gregory, et al., J. Med. Chem. 33:2569 (1990) and J. Med. Chem. 32:1673 (1989); C. J. Wang, et al., Tetrahedron 45:1323 (1989); and A.M. Slee, et al. Antimicrobial Agents and Chemotherapy 31:179 1 (1987) and D.C. Eustice, et al, Antimicrobial Agents and Chemotherapy 32:1218 (1988) are additional recent references disclosing 3-[(mono-substituted) phenyl]-2-oxazolidinones.

The following references disclose 3-[(di-substituted)phenyl]-, 3-[(tri-substituted)phenyl]- or 3-[(fused-ring substituted)phenyl]-2-oxazolidinones:

U.S. Pat. No. 4,977,173 discloses 3-phenyl-2-oxazolidinones having a lactam at the p-position and fluorine at the m-position of the phenyl ring (Formula XIII).

U.S. Pat. Nos. 4,921,869 and 4,801,600 disclose 6'-indolinyl- or alkanoneoxazolidinones (where the indolinyl nitrogen is meta to the oxazolidinone nitrogen).

U.S. Pat. No. 4,705,799 discloses substituted aminomethyloxooxazolidinyl benzene derivatives including sulfides, sulfoxides, sulfones and sulfonamides which possess antibacterial activity.

C.-H. Park, et al., J. Med. Chem. 35:1156 is an additional recent reference disclosing 3-[(di-substituted)phenyl]- and 3-[(tri-substituted)phenyl]-2-oxazolidinones.

European Pat. No. Publication 0 316 594 discloses substituted 3-(styryl)-2-oxazolidinones corresponding to U.S. Pat. No. 4,977,173 listed above.

European Pat. No. Publications 0 184 170 and 0 127 902 correspond to U.S. Pat. No. 4,705,799, discussed above.

PCT/US89/03548 and PCT/US90/06220 disclose 3-[(fused-ring substituted)-phenyl]- 2-oxazolidinones which are useful as antibacterial agents.

PCT/US92/08267 discloses substituted aryl- and heteroarylphenyloxazolidinones which are useful as antibacterial agents.

U.S patent application Ser. No. 07/880,492 filed May 8, 1992 discloses phenyloxazolidinones containing substituted diazine moieties.

None of the above cited references disclose the tropone substituted phenyloxazolidinones of the present invention.

SUMMARY OF THE INVENTION

A compound having the Formula

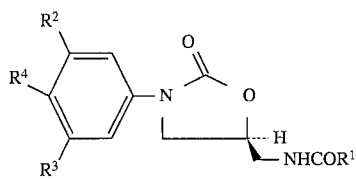

I wherein $R^1$ is
- (a) Hydrogen
- (b) $(C_1-C_8)$ alkyl optionally substituted with one or more of the following: F, Cl, hydroxy, alkoxy, acyloxy;
- (c) $(C_3-C_6)$ cycloalkyl
- (d) amino,
- (e) $(C_1-C_8)$ alkylamino,
- (f) $(C_1-C_8)$ dialkylamino,
- (g) $(C_1-C_8)$ alkoxy wherein $R^2$ and $R^3$ are the same or different and are selected from the group consisting of:
- (a) hydrogen
- (b) fluoro
- (c) chloro
- (d) $(C_1-C_8)$ alkyl
- (e) trifluoromethyl
- (f) hydroxy
- (g) $(C_1-C_8)$ alkoxy
- (h) nitro
- (i) amino with the proviso that when $R^2$ and $R^3$ are both other than hydrogen, then $R^2$ and $R^3$ are the same;

wherein $R^4$ is selected from the group consisting of

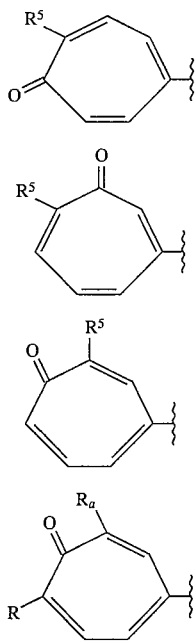

wherein R and $R_a$ are the same or different and are selected from the group consisting of $(C_1-C_8)$ alkyl optionally substituted with chloro, fluoro, hydroxy, $(C_1-C_8)$ alkoxy, amino, $(C_1-C_8)$ alkylamino, $(C_1-C_8)$ dialkylamino;

wherein $R^5$ is selected from the group consisting of hydrogen, $OR^6$, $SR^6$, $NHR^7$,

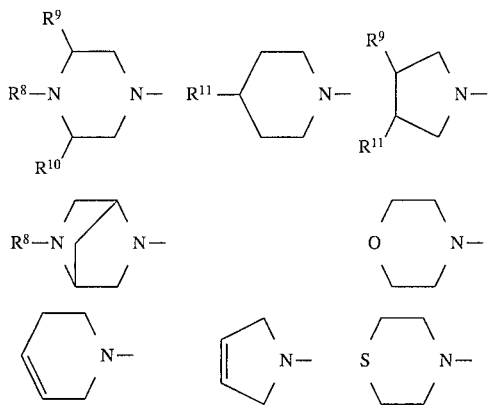

and $NR^7R^{12}$;

wherein $R^6$ is
- (a) hydrogen
- (b) $(C_1-C_8)$ alkyl optionally substituted with one or more halogens
- (c) $(C_1-C_8)$ alkyl optionally substituted with amino, $C_1-C_8$ alkylamino, $C_1-C_8$ dialkylamino
- (d) $(C_1-C_8)$ alkyl optionally substituted with one or more hydroxyls and with amino, alkylamino, dialkylamino
- (e) $(C_1-C_8)$ alkyl optionally substituted with one or more $C_1-C_8$ alkoxyls
- (f) $(C_2-C_8)$ alkenyl $(C_1-C_8)$ alkyl optionally substituted with amino, $(C_1-C_8)$ alkylamino, $(C_1-C_8)$ dialkylamino
- (g) $(C_2-C_8)$ alkynyl $(C_1-C_8)$ alkyl optionally substituted with amino, $(C_1-C_4)$ alkylamino, $(C_1-C_8)$ dialkylamino
- (h) $(C_2-C_8)$ acyl optionally substituted with hydroxyl, amino, $(C_1-C_8)$ alkylamino, $(C_1-C_4)$ dialkylamino
- (i) phenyl $(C_1-C_8)$ alkyl optionally substituted on phenyl with amino, $(C_1-C_8)$ alkylamino, $(C_1-C_8)$ dialkylamino
- (j) pyridyl $(C_1-C_8)$ alkyl optionally substituted on pyridyl with amino, $(C_1-C_8)$ alkylamino, $(C_1-C_8)$ dialkylamino
- (k) amino optionally substituted with one or two $(C_1-C_6)$ alkyl wherein $R^7$ is
- (a) hydrogen
- (b) $(C_1-C_8)$ alkyl optionally substituted by one or more chloro, fluoro, hydroxy, amino $(C_1-C_8)$ alkylamino, $(C_1-C_8)$ dialkylamino, phenyl, pyridyl, $(C_1-C_8)$ alkoxyl, $(C_1-C_8)$ alkoxycarbonyl moieties.
- (c) $(C_3-C_8)$ cycloalkyl optionally substituted with amino, $(C_1-C_8)$ alkylamino or $(C_1-C_8)$ dialkylamino
- (d) amino,
- (e) $(C_1-C_8)$ alkylamino
- (f) $(C_1-C_8)$ dialkylamino
- (g) hydroxyl
- (h) $(C_1-C_8)$ alkoxyl
- (i) $(C_2-C_8)$ alkenyl $(C_1-C_{10})$ alkyl optionally substituted with amino, $(C_1-C_4)$ alkylamino, $(C_1-C_4)$ dialkylamino
- (j) $(C_2-C_8)$ alkynyl $(C_1-C_{10})$ alkyl optionally substituted with amino, $(C_1-C_4)$ alkylamino, $(C_1-C_4)$ dialkylamino wherein $R^8$ is
(a) hydrogen
(b) $(C_1-C_8)$ alkyl
(c) $(C_3-C_8)$ cycloalkyl
(d) $(C_1-C_8)$ acyl
(e) $(C_1-C_8)$ alkoxycarbonyl
(f) $(C_1-C_8)$ alkylsulfonyl
wherein $R^9$ and $R^{10}$ maybe the same or different and are
(a) hydrogen
(b) $(C_1-C_8)$ alkyl
wherein $R^{11}$ is
(a) hydrogen
(b) hydroxy
(c) $(C_1-C_8)$ alkoxy
(d) amino
(e) alkylamino
(f) $(C_1-C_8)$ dialkylamino
(g) $(C_1-C_8)$ alkyl optionally substituted with amino $(C_1-C_4)$ alkylamino and $(C_1-C_4)$ dialkylamino;
wherein $R^{12}$ is $(C_1-C_8)$ alkyl;
and pharmaceutically acceptable salts and hydrates thereof.

The tropone-substituted phenyloxazolidinones Ia, Ib, Ic and Id contain at least one chiral center. It is apparent to those skilled in the art that when one chiral center is present, the compound can exist as one of two possible optical isomers [(R)- and (S)-enantiomers] or a racemic mixture of both. Both individual (R)- and (S)-enantiomers, as well as mixtures thereof, are within the scope of the tropone-substituted phenyloxazolidinones of the invention. In the event additional chiral centers are present, the resultant diastereomers, in racemic and enantiomerically enriched forms, are also within the scope of the antibacterial agents Ia, Ib, Ic and Id claimed in the invention.

The preferred absolute configuration of the oxazolidinones of this invention is as represented by generic structures Ia–Id. This absolute configuration is called (S) under the Cahn-Ingold-Prelog nomenclature system. It is this (S)-enantiomer which is the antibacterially-active optical isomer. The racemic mixture is useful in the same way and for the same purpose as the pure (S)-enantiomer; the difference is that twice as much racemic material must be used to produce the same antibacterial effect as the (S)-enantiomer.

The preferred embodiments of this invention are the oxazolidinones represented by generic structures Ia and Ib.

More preferred compounds are compounds Ia and Ib wherein $R^2$ is hydrogen and $R^3$ is hydrogen or flouro. The most preferred compounds are compounds Ia and Ib wherein both $R_2$ and $R_3$ are flouro and $R^1$ is methyl.

DETAILED DESCRIPTION OF INVENTION

The carbon atom content of various hydrocarbon-containing moieties is indicated by a prefix designating the minimum and maximum number of carbon atoms in the moiety; the prefix $(C_1-C_8)$ indicates a moiety of the integer "i" to the integer "j" carbon atom inclusive. Thus $(C_1-C_8)$ alkyl refers to alkyl of 1 to 4 carbon atoms inclusive, or methyl, ethyl, propyl, butyl, pentyl, hexyl, heptyl, octyl and isomeric forms thereof.

The term $(C_1-C_8)$ alkylamino means an amino moiety containing one alkyl moiety having 1 to 8 carbon atoms. The term $(C_1-C_8)$ dialkylamino means an amino-moiety containing two alkyl moieties having 1 to 8 carbon atoms. For example, propylamino and dipropylamino respectively.

The term optionally substituted with mean that the moiety can be substituted with 1 to 4 of the recited substituent. For example, $(C_1-C_8)$ alkyl optionally substituted with chloro, rioufo, hydroxy, $C_1-C_8$ alkoxy, amino, $(C_1-C_8)$ alkylamino, $(C_1-C_8)$ dialkylamino includes 1-chloropropyl, 1-fiuoropropyl 3-choloraproryl, 3-flouro propyl, 1-hydroxy butyl, 2-hydroxy butyl, 1-methoxypropyl 1-octlyloxy propyl, 1-amino propyl 1-aminooctyl; 1-butylaminopropyl; 1-dibutylaminopropyl and the like.

Preparation of the compounds of Formula Ia

Representative procedures for the preparation of compounds of this invention are outlined in Charts 1–7. Charts 1–4 depict the preparation of enantiomerically enriched tropone-substituted oxazolidinones. Charts 5–7 show routes to racemic intermediates and analogs. It will be apparent to those skilled in the art that these are merely representative procedures, and that slight modifications of the provided synthetic protocols will allow for the preparation of further examples of the tropone-substituted phenyloxazolidinones.

CHART 1

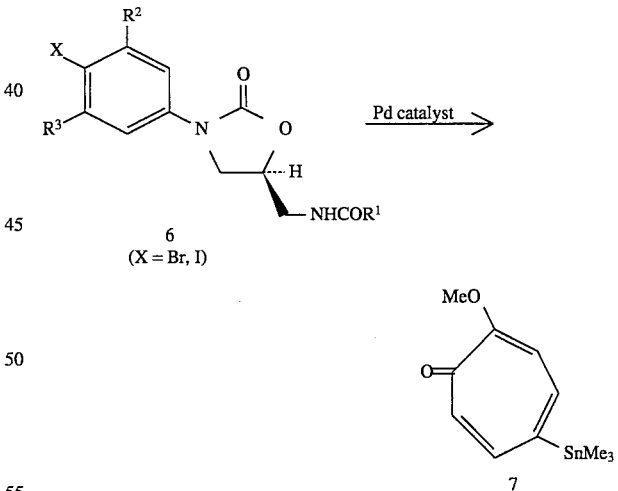

CHART 1 -continued

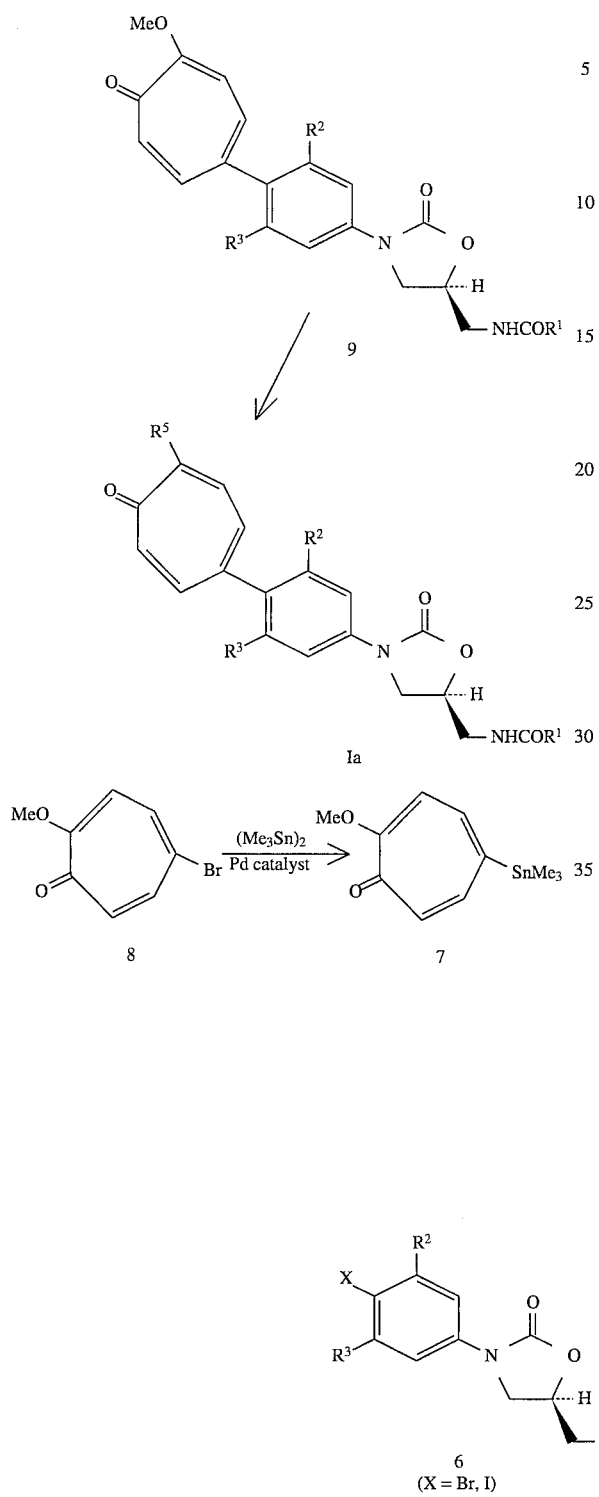

As shown in Chart 1, intermediate 6, (prepared as shown in Charts 3 and 4) is reacted with the novel tropone 7 (prepared from the known bromotropone 8, Banwell et al, Org. Prep. Proc. (1988) 393; Banwell et al, Tetrahedron Lett. (1985), 26, 4543, as shown at the bottom of Chart 1) in the presence of a suitable palladium catalyst such as tetrakis(triphenylphosphine)palladium or bis(triphenylphosphine)palladium chloride in a suitable solvent such as N,N-dimethylformamide (DMF) or 1,4-dioxane at a suitable temperature (typically 70°–100° C.) to furnish the coupled product 9. Compound 9 is an example of the tropone-substituted phenyloxazolidinones of structure Ia and can be further elaborated, if desired, by reacting 9 with a suitable nucleophile such as an amine in a suitable solvent system such as toluene or tetrahydrofuran/water at a suitable temperature (ambient to reflux temperature) to give additional examples of Ia. The methoxy group of compound 9 can also be replaced with alternative alkoxy residues by reacting 9 with the desired alcohol, usually in excess, in the presence of a catalytic amount of base, for example sodium hydride, to give the targeted adduct (see experimental section for an example). It will be apparent to one skilled in the art that the desired $R^1$ group may already be present on the tropone 7 prior to the palladium-mediated coupling step. It will also be apparent to one skilled in the art that variations in the bromotropone used (above references, Takaya, et al., J. Am. Chem. Soc. (1978), 100, 1778, etc.) and in the substituents of the various intermediates allows for the preparation of other enantiomerically enriched tropone-substituted phenyloxazolidinones of formulas Ia-d, which are the subject of this invention.

CHART 2

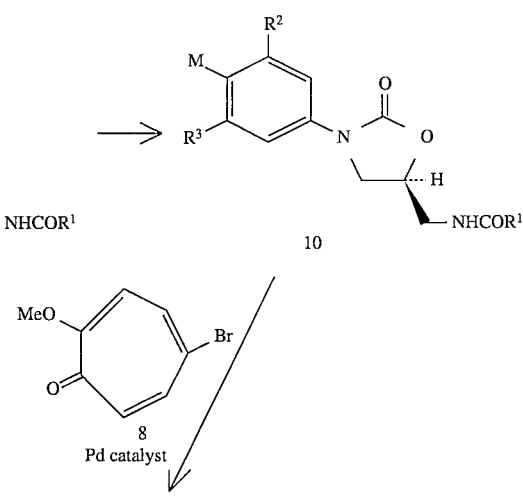

-continued
CHART 2

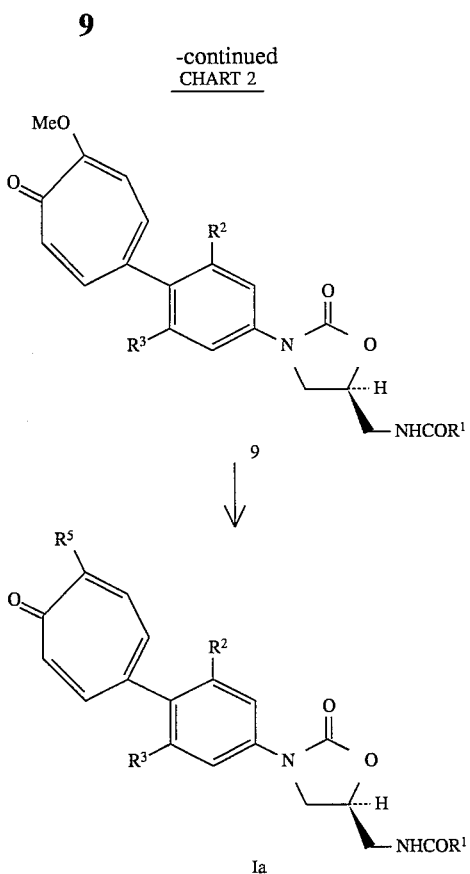

In Chart 2 is shown another synthetic alternative wherein the bromine or iodine of intermediate 6 (prepared as indicated in Charts 3 and 4) undergoes a halogen-metal exchange reaction to give the metallated derivative 10 (M=Me$_3$Sn or ZnX) which then undergoes a coupling reaction with the bromotropone 8 in the presence of a suitable palladium catalyst such as tetrakis(triphenylphosphine)palladium or bis(triphenylphosphine)palladium chloride in a suitable solvent such as N,N-dimethylformamide (DMF) or 1,4-dioxane at a suitable temperature (typically 70°–100° C.) to furnish the coupled product 9. If desired, compound 9 can then be further elaborated as described above.

CHART 3

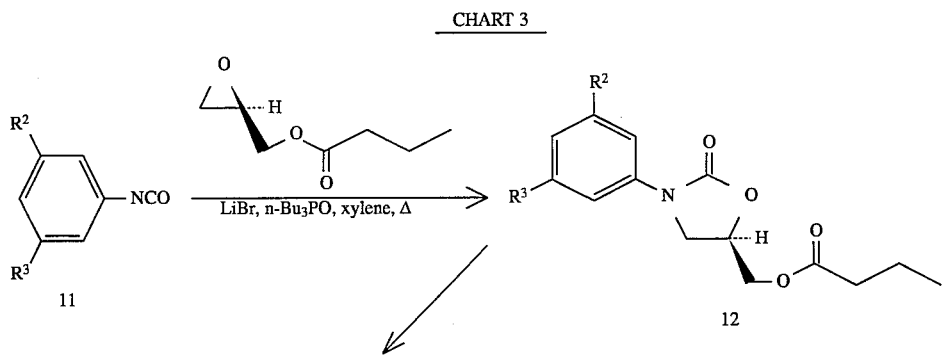

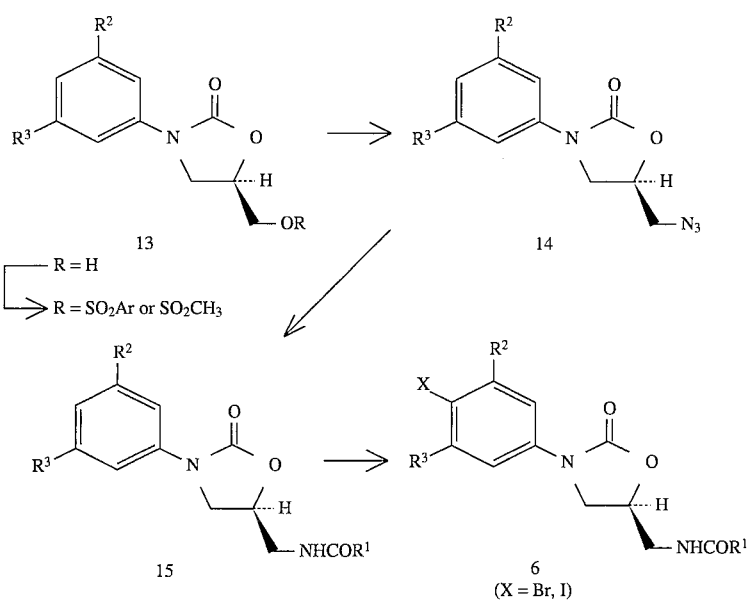

Chart 3 outlines the preparation of enantiomerically enriched intermediates of structure 6, which are needed (vide supra) for the preparation of optically active tropone-substituted phenyloxazolidinones Ia (see Charts 1 and 2) which are the subject of this invention. The key first step in this process involves the reaction of an optionally substituted phenyl isocyanate (11) with commercially available (−)-(R)-glycidyl butyrate, employing conditions first used by Herweh et al, Tetrahedron Lett. (1971), 809, to give the phenyloxazolidinone intermediate 12. The use of glycidyl butyrate in such a reaction to prepare oxazolidinone intermediates is disclosed in U.S. Pat. No. 4,705,799. Publications in the open literature have also appeared, e.g. Gregory et al., J. Med. Chem. (1989), 32, 1673. The butyryl group is then removed by reaction with an alkoxide, preferably sodium methoxide in methanol, to furnish the alcohol 13 (R═H). Compound 13 is then is then converted to the corresponding methylsulfonate (R═SO$_2$CH$_3$) or arylsulfonate (R═SO$_2$Ar) derivative, preferably the mesylate or tosylate, by the action of methanesulfonyl chloride/pyridine or methanesulfonyl chloride/triethylamine/dichloromethane or p-toluenesulfonyl chloride/pyridine. The resultant sulfonate is then reacted with azide such as sodium or potassium azide in an aprotic solvent such as DMF or 1-methyl-2-pyrrolidinone optionally in the presence of a catalyst such as 18-crown-6 at a temperature of 50° to 90° C. to afford the azide 14. The azide 14 is then reduced by hydrogenation with palladium on carbon or a platinum catalyst in an appropriate solvent such as ethyl acetate or methanol. Alternatively, the azide may be reduced by treatment with a trivalent phosphorus compound such as triphenylphosphine in the presence of water and in a suitable solvent such as tetrahydrofuran (THF). The aminomethyl compound obtained by reduction of the azide 14 is then acylated by reactions known to those skilled in the art to give the intermediates of structure 15. For example, the amine can be reacted with an acid chloride or anhydride in a basic solvent such as pyridine at a temperature ranging from −30° to 50° C. to provide the acylated intermediate 15 where R$^1$=optionally substituted alkyl. It will be apparent to one skilled in the art that the other acyl groups of this invention can be readily appended to the aminomethyl intermediate by standard acylation techniques known to those skilled in the art. Intermediate 15 is iodinated with iodine monochloride in acetic acid/trifluoroacetic acid at a temperature from 0° to 70° C. or with iodine and silver trifluoroacetate to give the enantiomerically enriched iodophenyloxazolidinone intermediate 6 (X═I). Alternatively, 15 can be brominated with N-bromosuccinimide to give the brominated congener 6 (X═Br).

CHART 4

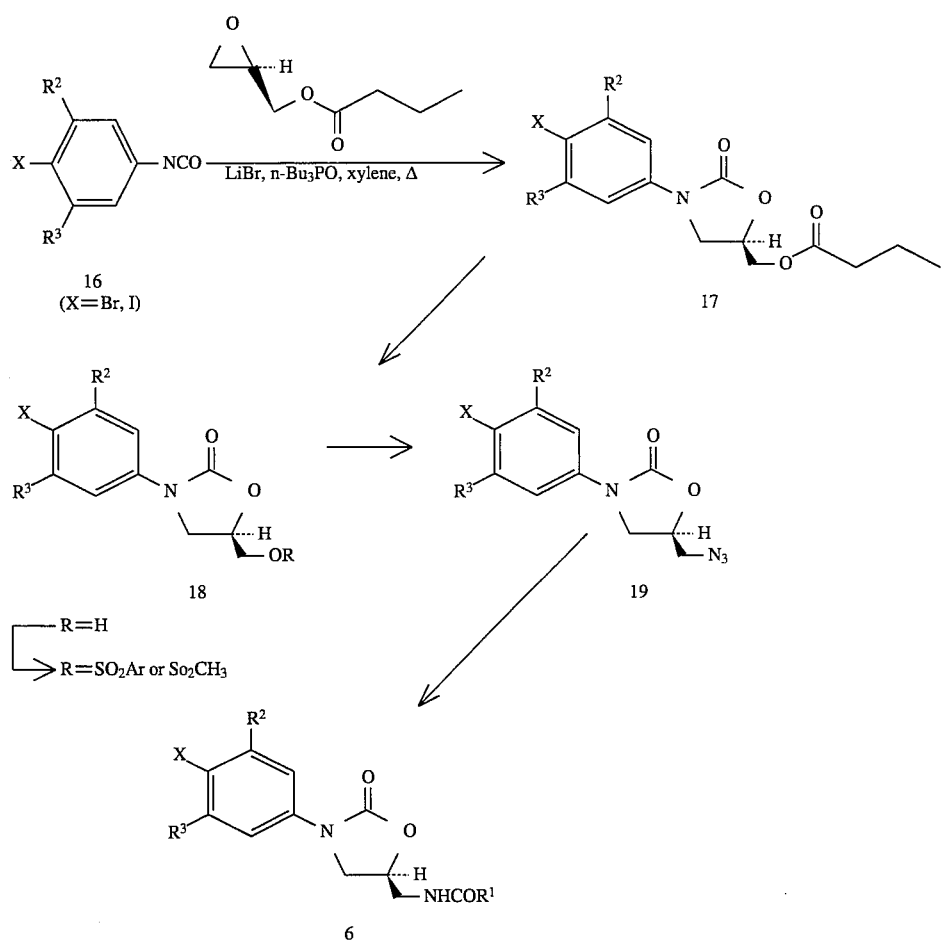

Chart 4 depicts a variation of the synthetic protocol described in Chart 3 wherein the iodine or bromine moiety (X) of structure 6 is already present in the aryl isocyanate 16 used in the first step of the sequence. Utilizing the reactions described in Chart 3 (vide supra), the aryl isocyanate 16 is first converted to the oxazolidinone 17, and subsequently to the derivatives 18 and 19. The azide 19 is then reduced by reacting it with a trivalent phosphorus compound such as triphenylphosphine in the presence of water and in a suitable solvent such as THF. Acylation of the resultant aminomethyl intermediate then affords the enantiomerically enriched compound 6.

CHART 4a

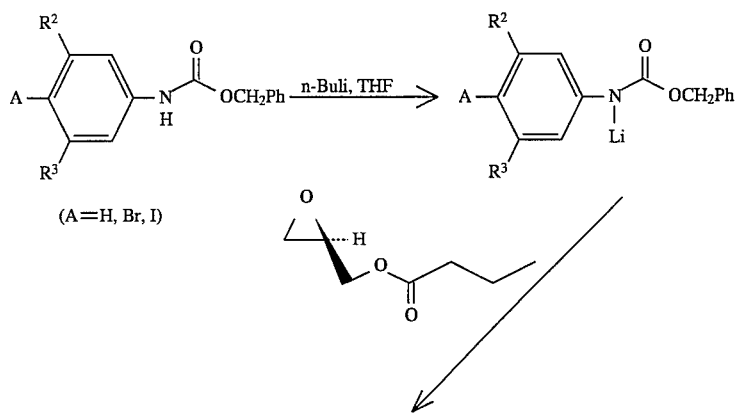

-continued
CHART 4a

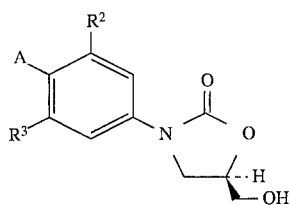

13 (A=H)
18 (A=Br, I)

Chart 4a depicts an alternative preparation of enantiomerically enriched intermediates of structure 13 (see Chart 3) and 18 (see Chart 4). In this sequence, an appropriate Cbz-protected aniline, readily prepared by standard Schotten-Baumann conditions or other variations known to one skilled in the art, is deprotonated with n-butyllithium in a suitable solvent such as tetrahydrofuran and at a suitable temperature such as −78° to 68° C. The addition of commercially available (−)-(R)-glycidyl butyrate, followed by warming to ambient temperature, then directly affords the hydroxymethyl-substituted phenyloxazolidinone intermediates 13 (A=H) and 18 (A=Br, I). Compounds 13 and 18 can be readily converted to enantiomerically enriched tropone-substituted phenyloxazolidinones of formula Ia to Id employing procedures outlined in Charts 1–4.

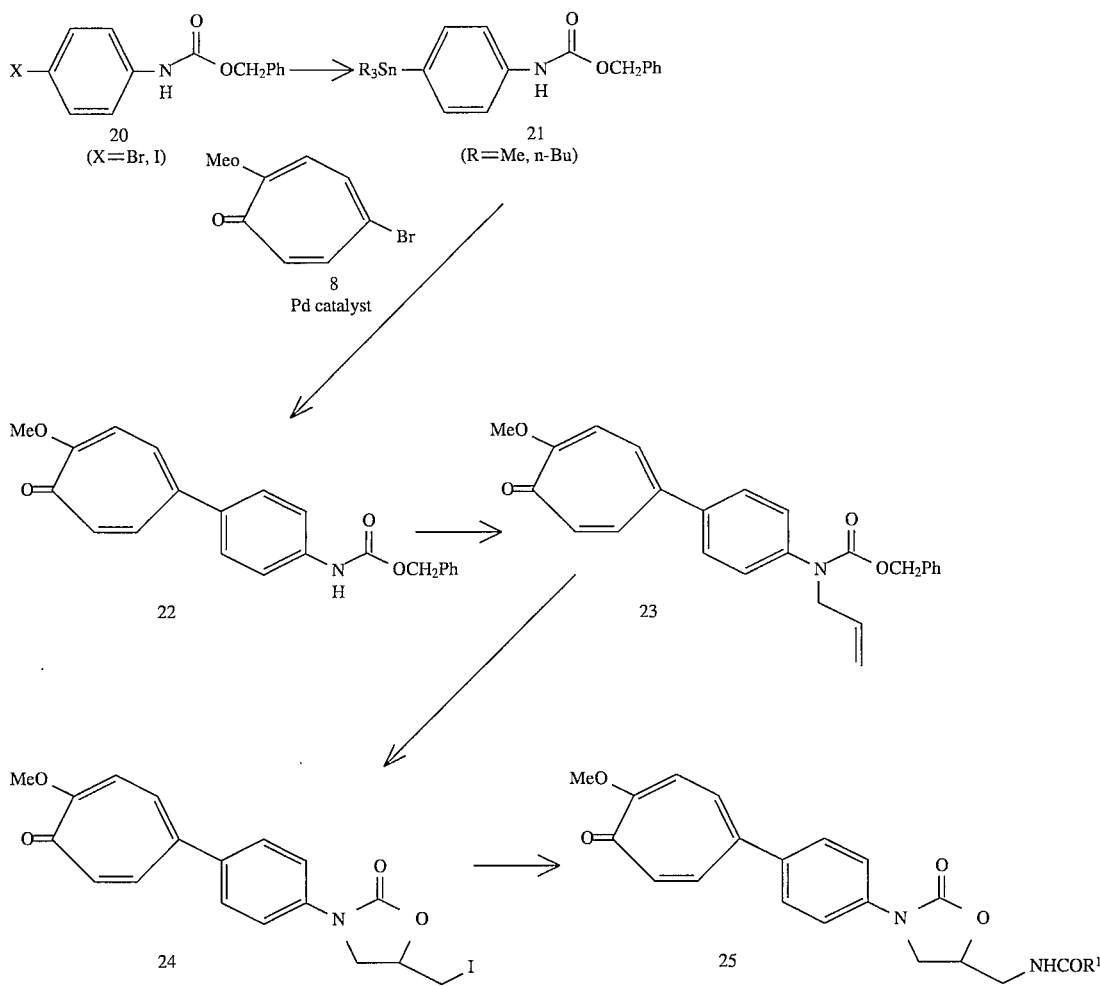

Chart 5 depicts a route to racemic tropone-substituted oxazolidinone antibacterial agents. In a representative example, the Cbz derivative 20 (X=Br), prepared from 4-bromoaniline under standard Schotten-Baumann conditions, was treated with two equivalents of n-butyllithium in THF at −78° to −40° C. and then quenched with tributyltin chloride to give the tin derivative 21 (R=n-Bu). Compound 21 was then reacted with the bromotropone 8 in the presence of a suitable palladium catalyst such as tetrakis(triphenylphosphine)palladium or bis(triphenylphosphine)palladium chloride in a suitable solvent such as N,N-dimethylformamide (DMF) or 1,4-dioxane at a suitable temperature (typically 70°–100° C.) to furnish the coupled product 22. Allylation of 22 was accomplished by deprotonation with a suitable base such as sodium hydride in a suitable solvent such as THF and then treating the reaction mixture with allyl bromide optionally in the presence of a catalytic iodide source such as tetrabutylammonium iodide at ambient to reflux temperature to afford 23. Intermediate 23 was subjected to a Cardillo-Ohno cyclocarbamation reaction involving treatment of 23 with iodine in a suitable solvent such as chloroform and at a suitable temperature, typically ambient temperature, to provide the iodomethyloxazolidinone 24, Cardillo et al, Tetrahedron (1987), 43,2505, Ohno et al., Tetrahedron Lett. (1987), 28, 3123. Compound 24 can then be converted to 25, which is an example of analogs of structure Ia, by a sequence of three reactions. These include azide displacement, reduction to the corresponding aminomethyloxazolidinone, and acylation, all carried-out as described above. It will be apparent to one skilled in the art that reasonable variations in the substituents of the various residues allows for the preparation of other racemic troponesubstituted phenyloxazolidinones of formulas Ia–d, which are the subject of this invention.

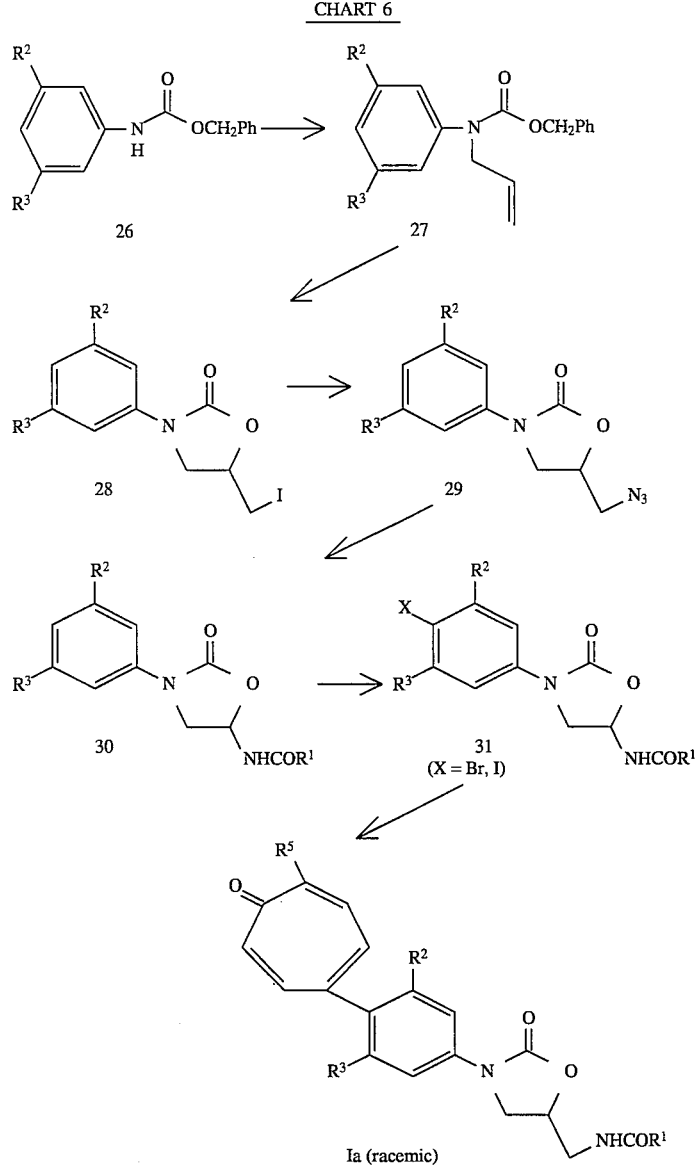

CHART 6

Chart 6 outlines another synthetic approach to racemic oxazolidinones of structure Ia which can be viewed as a hybrid of Charts 1, 2, and 5. The Cbz derivative 26, prepared from the corresponding aniline via standard Schotten-Baumann conditions, is first allylated by deprotonation with a suitable base such as sodium hydride in a suitable solvent such as THF and then treating the reaction mixture with allyl bromide optionally in the presence of a catalytic iodide source such as tetrabutylammonium iodide at ambient to reflux temperature to afford 27. Intermediate 27 was subjected to a Cardillo-Ohno cyclocarbamation reaction involving treatment of 27 with iodine in a suitable solvent such as chloroform and at a suitable temperature, typically ambient temperature, to provide the iodomethyloxazolidinone 28. The iodide 28 is then reacted with a source of azide such as sodium or potassium azide in an aprotic solvent such as DMF or 1-methyl-2-pyrrolidinone optionally in the presence of a catalyst such as 18-crown-6 at a temperature of 50° to 90° C. to afford the azide 29. The azide 29 is then reduced by hydrogenation with palladium on carbon or a platinum catalyst in an appropriate solvent such as ethyl acetate or methanol. Alternatively, the azide may be reduced by treatment with a trivalent phosphorus compound such as triphenylphosphine in the presence of water and in a suitable solvent such as tetrahydrofuran (THF). The aminomethyl compound obtained from the azide 29 is then acylated by reactions known to those skilled in the art to give the intermediates of structure 30. Bromination or iodination of the phenyl ring of 30, employing conditions noted above for the preparation of optically active intermediate 6, then affords the racemic compound 31. Intermediates of structure 31 can be elaborated to racemic troponesubstituted phenyloxazolidinones of formula Ia by the same techniques utilized to convert enantiomerically enriched intermediates of structure 6 to Ia (see Charts 1 and 2). It will be apparent to one skilled in the art that reasonable variations in the substituents of the various residues allows for the preparation of other racemic tropone-substituted phenyloxazolidinones of formulas Ia–d, which are the subject of this invention.

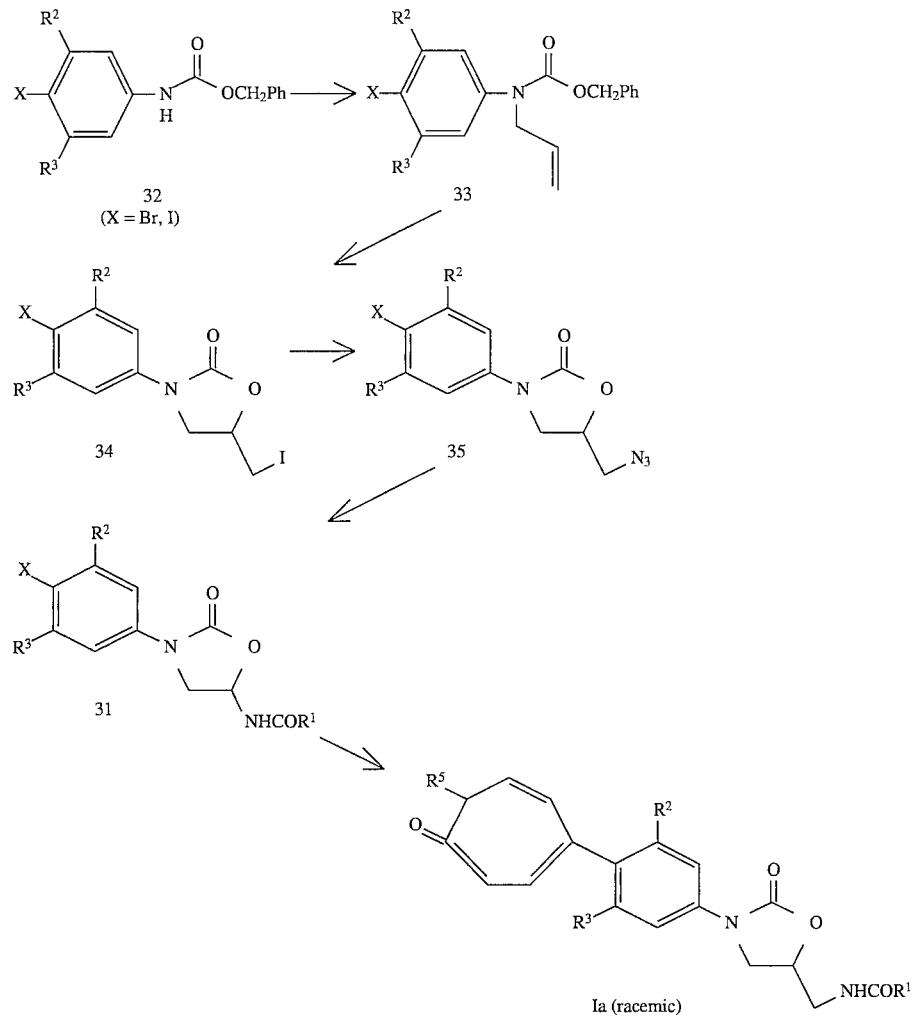

CHART 7

Chart 7 describes a variation of the scheme shown in Chart 6 wherein the bromine or iodine atom of structure 31 is already present in the Cbz-substituted starting material 32. Allylation of 32 as described above affords the adduct 33. Iodocyclocarbamation of 33 under the usual Cardillo-Ohno conditions then furnishes the iodomethyloxazolidinone intermediate 34. Azide displacement provides the azidomethyl oxazolidinone 35 which is reduced by reacting it with a trivalent phosphorus compound such as triphenylphosphine in the presence of water and in a suitable solvent such as THF. Acylation of the resultant aminomethyl intermediate then affords the racemit compound 31, which can be readily converted to raeemie Ia. Minor modifications of this protocol will allow one skilled in the art to prepare additional examples of the oxazolidinones Ia–d.

The starting materials utilized in the processes of Charts 1 to 7 are all either commercially available or can be readily made by methods known in the prior art.

The invention includes pharmaceutically acceptable acid addition salts of compounds of Formula I when a basic group is present, such as an amino residue. Especially preferred are those salts made from mineral acids (HCl, HBr, $H_3PO_4$, $H_2SO_4$, etc.), organic sulfonie acid (methanesulfonie acid, p-toluenesulfonie acid, etc.), and organic earboxylic acids (acetic acid, succinic acid, tartaric acid, citric acid, lactic acid, maleic acid, oxalic acid, etc.; amino acids; carbohydrate acids such as gluconic and galacturonic acids, etc.) salts. Also included are pharmaceutically acceptable base addition salts of the compound of Formula I when an acidic group is present, such as a carboxylic acid or when $R^1$ is a hydroxyl group. Such salts include the following cations but are not limited to these: alkali metal ions such as potassium, sodium, lithium; alkaline earth metal ions such as magnesium or calcium; ammonium ions such as ammonium, tetrabutylammonium and pyridinium.

The compounds of this invention may be administered orally, topically or parenterally. Generally, such antibacterially effective amount of dosage of active component will be in the range of about 0.1 to 100, more preferably about 3 to about 50 mg/kg of body weight/day depending upon the weight, age and condition of the patient. This dose can preferably be given in divided doses and administered 2–4 times daily. The preferred route of administration as well as the particular dosage form for either the parenteral or oral route depends on the particular facts of the situation including the nature of the infection (particular microorganism involved, its virulence, the extent of the infection and the age, weight, sex and general physical condition of the patient. The usual pharmaceutical dosage forms appropriate for parenteral (solution, suspension in oil) and oral (tablet, capsule, syrup, suspension, etc.) administration are known to those skilled in the art and there is nothing unusual about using those dosage forms with the Tropone-substituted phenyloxazolidinones of Formula I.

The in vitro antibacterial activity of various compounds of this invention against *Staphylococcus aureus* was determined by methods known in the art and are shown in Table 1. These are antibacterial agents useful for treating infections in mammals (humans and animals such as cattle, horses, sheep, dogs, cats, etc.) caused by gram-positive and anaerobic organisms. The tropone-substituted phenyloxazolidinones of Formula I are also useful in treating patients infected with one or more Mycobacterium spp. Of particular interest, the compounds Ia–Id of the invention are useful in treating patients infected with *M. tuberculosis* and *M. avium*.

The tropone substituted-phenyloxazolidinones of Formula I can be used either alone or in combination with other antibacterial or non-antibacterial agents as is known to those skilled in the art.

EMBODIMENTS OF THE INVENTION

Preparation 1 Tri-n-butyl[4-(carbobenzyloxyamino)phenyl] tin

N-Cbz-4-bromoaniline (3.08 g, 11.2 mmol) was dissolved into 50 ml of anhydrous THF and the solution was cooled to −78° C. via a dry-ice/acetone bath. Next a solution of n-butyllithium (1.6M in hexanes, Aldrich, 23.52 mmol) was added over 5 minutes. The solution became a deep yellow color. The solution was stirred for 10 minutes and was quenched with tri-n-butyltin chloride (3.83 g, 11.76 mmol). The yellow slurry became a colorless solution. After stirring for 30 minutes and warming to −20° C., the reaction was quenched with saturated aqueous $NH_4Cl$ (50 ml). The reaction mixture was poured into a separatory funnel along with 250 ml of ether and 100 ml of water. The mixture was shaken and the organic phase separated and dried over anhydrous $Na_2SO_4$, filtered and concentrated to give an oil that was purified by chromatography on silica gel (eluted with 20:1 hexane/ether). Isolated 2.99 g of the title compound as a colorless oil.

MS(EI): m/z (rel int.): 460(25), 404(5), 227, 91(100). $^1H$ NMR $CDCl_3$): δ7.48–7.31 (m, 9H), 5.19 (s, 2H), 1.55–1.47 (m, 6H), 1.38–1.26 (m, 6H), 1.03 (t, 6H, J=8.33 Hz), 0.877 (t, 9H, J=7.26 Hz).

Preparation 2 N-(Carbobenzyloxy)-4-(4-methoxy-5-oxo-1,3,6-cycloheptatrien-1-yl)aniline The Tri-n-butyl[4-(carbobenzyloxyamino)phenyl]tin (726mg, 1.4 mmol) was dissolved into 10 ml of 1,4-dioxane and 5-bromo-2-methoxycyclohepta-2,4,6-trien-1-one (215 mg, 1.0 mmol) was added. The resulting slurry was degassed by evacuation and flushing with $N_2$ (3 times). The catalyst bis(triphenylphosphine)palladium(II) chloride was added and the mixture was heated to reflux under $N_2$. Progress was monitored by TLC. The reaction was shown to be complete after 2 h. The reaction was cooled to ambient temperature and concentrated under reduced pressure. The residue was slurried into 75 ml of $CH_2Cl_2$ and was stirred with saturated aqueous KF (75 ml) for 15 minutes. The organic phase was separated and washed with water (50 ml) and brine (50 ml). The organic phase was dried over anhydrous $Na_2SO_4$, filtered and concentrated to give a yellow solid that was purified by radial chromatography (eluting with 1:1 $CHCl_3$/EtOAc with 1% MeOH). This gave 361 mg of the title compound as a yellow solid.

MP: 193°–195° C.

HRMS (EI): [M]+, calculated for $C_{22}H_{19}N_2O_4$: 361/1314; found: 361.1311. $^1H$ NMR ($CDCl_3$): δ7.54–7.23 (m, 6H), 6.84 (d, 2H), 5.23 (s, 1H), 3.98 (s, 3H).

Preparation 3 N-(2-propenyl)-N-(carbobenzyloxy)-4-(4-methoxy-5-oxo- 1,3,6-cycloheptatrien-1-yl)aniline.

The N-(Carbobenzyloxy)-4-(4-methoxy-5-oxo-1,3,6-cycloheptatrien-1-yl )aniline (195 mg, 0.54 mmol) was slurried into 5 ml of dry THF and a 50% oil suspension of NaH was added. Gas evolution was observed. The mixture was allowed to stir at ambient temperature under $N_2$ for 20 minutes and allyl bromide was added along with tetra-n-butylammonium iodide. The mixture was allowed to stir at ambient temperature under $N_2$. After 3.5 hrs. TLC showed that 6 was consumed. Excess NaH was consumed by the addition of pH 7 phosphate buffer (25 ml). The mixture was poured into a separatory funnel along with 25 ml of water and the aqueous phase was extracted with $CH_2Cl_2$ (2×25 ml). The combined organic phases were dried over anhydrous $Na_2SO_4$. The oil obtained after concentration of the organic phase was purified by radial chromatography (eluted with 1% MeOH/$CHCl_3$ {300 ml} and 2% MeOH/$CHCl_3$ {100 ml}). This gave 198 mg of the title compound as an oil that solidifed upon standing.

HRMS (EI): [M]+, calculated for $C_{25}H_{23}NO_4$: 401.1627; found: 401.1630.

$^1H$ NMR ($CDCl_3$): δ7.52 (dd, 1H, J=12.6 Hz), 7.46–7.42 (m, 2H), 7.34–7.33 (m, 8H), 7.26 (dd, 1H, J=10.6 Hz), 6.845 (d, 1H, J=10.6 Hz), 5.93 (m, 1H), %.20–5.18 (bs, 3H), 5.15–5.14 (m, 1H), 4.32 (d, 2H, J+5.6 Hz), 3.99 (s, 3H).

Preparation 4 (±)-5-(Iodomethyl)-3-[4-methoxy-5-oxo-1,3,6-cycloheptatrien- 1-yl)phenyl]-2-oxazolidinone The N-(2-propenyl)-N-(carbobenzyloxy)-4-(4-methoxy-5-oxo- 1,3,6-cycloheptatrien-1-yl)aniline (180 mg, 0.449 mmol) was dissolved into 8 ml of chloroform and $I_2$ (285 mg, 1.12 mmol) was added. The mixture became a grape purple color and was stirred at ambient temperature under $N_2$. After 20 hours of reaction time TLC showed 7 was consumed with the formation of a new lower $R_f$ product. The reaction mixture was poured into a separatory funnel along with 50 ml of CHCl$_3$, and the solution was washed with a 20% aqueous solution of sodium thiosulfate (25 ml). The organic phase was separated, dried over anhydrous Na$_2$SO$_4$, filtered and concentrated to give the title compound as an orange solid that was purified by radial chromatography (eluting with 200 ml of 1% MeOH/CHCl$_3$ and 200 ml of 2% MeOH/CHCl$_3$). Isolated 139 mg of the title compound as a light yellow solid.

MP: 194°–196° C.

Anal. calcd for C$_{18}$H$_{16}$NO$_4$I: C, 49.45; H, 3.69; N, 3.20. Found: C, 49.03; H, 3.62; N, 3.00.

HRMS: calcd for C$_{18}$H$_{16}$INO$_4$: 437.0126. Found: 437.0110.

$^1$H NMR (CDCl$_3$): δ7.65 (d, 2H, j=8.8 Hz), 7.55 (dd, 1H, J=11.5, 12.6 Hz), 7.52 (d, 2H, J=8.8 Hz), 7.34 (d, 1H, J=10.4 Hz), 7.28 (d, 1H, J=11.5 Hz), 6.88 (d,1H, j=10.6 Hz), 4.79 (m, 1H, 4.24 (t, 1H, J=8.9 Hz), 4.00 (s, 3H), 3.855 (dd, 1H, J=9.2 Hz), 3.505 (dd, 1H, J=14.5 Hz), 3.395 (dd, 1H, J=10.4 Hz).

Preparation 5 (±)-5-(Azidomethyl)-3-[4-(4-methoxy-5-oxo-1,3,6-cycloheptatrien- 1-yl)phenyl-2-oxazolidinone The (±)-5-(Iodomethyl)-3-[4-methoxy-5-oxo-1,3,6-cycloheptatrien-1-yl)phenyl]- 2-oxazolidinone (125 mg, 0.286 mmol) was dissolved into 6 ml of dry DMF and sodium azide (93mg, 1.43 mmol) was added along with 18-Cr-6 (10mg). The mixture was heated to 60° C. under N$_2$ and progress was monitered by TLC. After 2 hours TLC showed 8 was consumed. The reaction was cooled to ambient temperature and DMF was removed under reduced pressure. The residue that remained was slurried into CHCl$_3$ (75 ml) and the salts were removed by washing with water (2×30 ml). The organic phase was separated and washed with brine (30 ml). The organic phase was dried over anhydrous sodium sulfate, filtered and concentrated to give 105mg of the title compound as a yellow solid. This material was sufficiently pure to carryon without any further purification.

MP: 170°–171° C.

Anal. calcd for C$_{18}$H$_{16}$N$_4$O$_4$: C, 61.36; H, 4.58: N, 15.90. Found: C, 61.08; H, 4.52; N, 15.75.

HRMS: calcd for C$_{18}$H$_{16}$N$_4$O$_4$: 352.1171. Found: 352.1169. $^1$H NMR (CDCl$_3$): δ7.645 (d, 2H, J=8.8 Hz), 7.545 (dd, 1H, J=16, 12.5 Hz), 7.515 (d, 2H, J=8.8 Hz), 7.34 (d, 1H, J=12.5 Hz), 7.285 (dd, 1H, J=10.6 Hz), 6.88 (d, 1H, J=10.6 Hz), 4.84–4.85 (m, 1H), 4.16 (t, 1H, J=8.9 Hz), 4.00 (s, 3H), 3.91 (dd, 1H, J=8.9 Hz), 3.755 (dd, 1H, J=13.2 Hz), 3.625 (dd, 1H, J=13.2 Hz).

Preparation 6 Trimethyl(4-methoxy-5-oxo-1,3,6-cycloheptatrien-1-yl)tin.

Hexamethylditin (305 mg, 0.930 mmol) was dissolved into 5 ml of 1,4-dioxane and the solution was degassed by evacuation and flushing with N$_2$ (3 times). The bromotropone 8 (200 mg, 0.930 mmol) was added along with the catalyst bis(triphenylphosphine)palladium(II) chloride (16.3 mg, 2.5 mol%) was added. The mixture was degassed a final time and heated to reflux under N$_2$. The reaction was monitored by TLC. The reaction mixture darkened upon warming. After 1.5 hours TLC showed that 3 was consumed. The reaction mixture was cooled to ambient temperature and concentrated under reduced pressure. This gave a black oil that was purified by chromatography on silica gel (eluting with 1:1 EtOAc/CHCl$_3$ with 1% MeOH). This gave the title compound (239 mg) as an oil that solidired upon standing in the freezer.

MP: 60°–61° C.

HRMS: Calcd for C$_{11}$H$_{16}$O$_2$Sn: 300.0170. Found: 300.0159.

$^1$H NMR (CDC$_3$l): δ7.36 (d, 1H, J=11.8 Hz), 7.23 (d, 1H, j+9.6 Hz), 7.15 (d, 1H, J=11.8 Hz), 6.725 (d, 1H, J=9.6 Hz), 3.94 (s, 3H), 0.32 (s, 9H), $^{119}$Sn J=129.3 Hz, $^{117}$Sn J=55.2 Hz, $^{115}$Sn J=52.9 Hz).

Preparation 7 (R)-[3-(3-fluorophenyl)-2-oxo-5-oxazolidinyl]methyl butyrate.

A mixture of lithium bromide (0.181 g, 2.08 mmol), tri-n-butylphosphine oxide (0.454 g, 2.08 mmol), and dry o-xylene (10 mL) was azeotropically dried for 1 h. After cooling below the reflux point, a solution of (R)-glycidyl butyrate (5.000 g, 34.68 mmol) and 3-fluorophenyl isocyanate (4.755 g or 3.96 mL, 34.68 mmol) in dry o-xylene (10 mL) was added over 10 min to the hot solution (some refluxing observed during the addition). When the addition was completed, the solution was heated to reflux for 2 h and then allowed to cool to room temperature. The solvent was removed in vacuo and the residue chromatographed over silica gel, eluting with hexane/ethyl acetate (6:1, 4:1, and then 2:1), to afford 8.758 g (90%) of the title compound as a colorless syrup with the following characteristics:

$[α]^{25}_D$ –46.7° C. (c 1.0, CHCl$_3$).

IR (mineral oil mull) 1758, 1615, 1591, 1498, 1229, 1197, 1169 cm$^{-1}$.

$^1$H-NMR (CDCl$_3$, 300 MHz) δ7.44 ("dt", J=11.2, 2.3 Hz, 1H), 7.34 ("dt", J=8.3, 6.5 Hz, 1H), 7.23 (ddd, J=8.3, 2.1, 0.9 Hz, 1H), 6.86 (dddd, J=8.2, 8.2, 2.5, 0.9 Hz, 1H), 4.88 (m, 1H), 4.39 (dd, J=12.3, 3.8 Hz, 1H), 4.32 (dd, J=12.3, 4.7 Hz, 1H), 4.13 ("t", J=9.0 Hz, 1H), 3.82 (dd, J=9.0, 6.1 Hz, 1H), 2.33 (t, J=7.3 Hz, 2 H), 1.63 (m, 2H), 0.92 (t, J=7.4 Hz, 3H).

MS m/z (relative intensity) 281 (33.1, M$^+$), 193 (9.9), 180 (3.3), 150 (28.7), 148 (68.6), 137 (59.3), 123 (41.7), 95 (38.3), 43 (100).

HRMS m/z 281.1068 (calcd for C$_{14}$H$_{16}$FNO$_4$: 281.1063).

Anal. calcd for C$_{14}$H$_{16}$FNO$_4$: C, 59.78; H, 5.73; N, 4.98. Found: C, 59.98; H, 5.72; N, Preparation 8 (R)-3-(3-fluorophenyl)-5-(hydroxymethyl)-2-oxooxazolidine.

A solution of the (R)-[3-(3-fluorophenyl)-2-oxo-5-oxazolidinyl]methyl butyrate (2.789 g, 9.91 mmol) in methanol (10 mL) was treated with a 25 wt. % solution of sodium methoxide in methanol (57 μL, 0.99 mmol) at ambient temperature. After 45 min TLC (5% MeOH/CHCl$_3$) revealed the starting material was consumed. The reaction mixture was carefully quenched by the addition of 1N HCl (0.99 mL, 0.99 mmol) and then concentrated in vacuo. Chromatography of the crude product over silica gel, eluting first with 1:1 hexane/ethyl acetate and then ethyl acetate, afforded 1.903 g (91%) of the title compound as a white solid with the following characteristics:

mp 106.5°–107.5° C.

$[α]^{25}_D$ –66.8° (c 1.1, CH$_3$CN).

IR (mineral oil mull) 3520, 1724, 1612, 1590, 1496, 1428, 1420, 1232, 1199 cm$^{-1}$.

$^1$H-NMR (CDCl$_3$, 300 MHz) δ7.44 ("dt", J=11.3, 2.3 Hz, 1H), 7.32 ("dt", J=8.3, 6.5 Hz, 1H), 7.23 (ddd, J=8.3, 2.1, 1.0 Hz, 1H), 6.84 (dddd, J=8.2, 8.2, 2.5, 1.0 Hz, 1H), 4.77 (m, 1H), 4.07–3.96 (m, 3H), 3.76 (dd, J=12.7, 3.9 Hz, 1H), 2.44 (br s, 1H).

MS m/z (relative intensity) 211 (100, M$^{+)}$, 180 (6.8), 136 (34.3), 124 (84.7), 95 (71.6).

HRMS m/z 211.0641 (calcd for C$_{10}$H$_{10}$FNO$_3$: 211.0645).

Anal. calcd for C$_{10}$H$_{10}$FNO$_3$: C, 56.87; H, 4.77; N, 6.63. Found: C, 56.85; H, 4.94; N, 6.56.

The enantiomeric excess of the oxazolidinone alcohol was determined by reacting it with (R)-(+)-α-methoxy-α-(trifluoromethyl)phenylacetic acid (DCC, DMAP, CH$_2$Cl$_2$, rt) and examining the $^1$H-NMR spectrum of the resultant Mosher ester. The % ee was estimated to be ≧95%.

Preparation 9 (R)-3-(3-fluorophenyl)-5-(hydroxymethyl)-2-oxooxazolidine.

A solution of N-(carbobenzyloxy)-3-fluoroaniline (1.000 g, 4.08 mmol) in dry tetrahydrofuran (10 mL) was cooled with a dry ice/acetone bath to ca. −78° C. and then n-butyllithium (1.87 mL of a 1.6M solution in hexanes, 2.91 mmol) was added. (R)-glycidyl butyrate (0.420 g or 0.413 mL, 2.91 mmol) was then added via syringe and the cooling bath allowed to dissipate overnight, with the reaction mixture reaching ambient temperature. The reaction mixture was quenched by the careful addition of saturated aqueous ammonium chloride, the entire mixture transferred to a separatory funnel with dichloromethane washings, and the mixture extracted with dichloromethane. The combined organic extracts were dried over sodium sulfate, filtered and concentrated in vacuo to give an oil which was purified by chromatography over silica gel, eluting with 10% acetonitrile/chloroform containing 1% methanol, to afford 0.555 g (90% based on glycidyl butyrate) of the title compound as a white solid identical in all respects to an authentic sample obtained as described in the previous experimental procedure.

Preparation 10 (R)-[3-(3-fluorophenyl)-2-oxo-5-oxazolidinyl]methyl 4-methylbenzenesulfonate.

A solution of (R)-3-(3-flourophenyl)-5-(hydroxymethyl)-2-oxooxazolidine (1.800 g, 8.52 mmol) in dry pyridine (10 mL) was cooled to ca. 5° C. and then treated with p-toluenesulfonyl chloride (1.706 g, 8.95 mmol). The solution was left at this temperature overnight. TLC (5% methanol/chloroform or 1:1 hexane/ethyl acetate) indicated the starting material was consumed. The reaction mixture was dumped into ice water (30 mL) and the resultant precipitate collected by vacuum filtration through a medium-porosity sintered glass funnel. The collected solids were thoroughly washed with cold water, dried in vacuo, and recrystallized from ethyl acetate/hexane to give 2.743 g (88%) of the title compound as a white solid with the following characteristics:

mp 114°–115° C.

$[a]^{25}_D$ −62.6° (c 1.0, $CH_3CN$).

IR (mineral oil mull) 1751, 1617, 1591, 1499, 1415, 1362, 1227, 1202, 1191, 1172, 1093, 967 $cm^{-1}$.

$^1$H-NMR ($CDCl_3$, 300MHz) δ7.78 ("d", J=8.4 Hz, 2H), 7.38 ("dt", J=11.2, 2.3 Hz, 1H), 7.36 "d", J=7.8 Hz, 2H), 7.33 ("dt", J=8.3, 6.6 Hz, 1H), 7.16 (ddd, J=8.3, 2.2, 1.0 Hz, 1H), 6.86 (dddd, J=8.2, 8.2, 2.5, 1.0 Hz, 1H), 4.84 (m, 1H), 4.29 (dd, J=11.1, 4.1 Hz, 1H), 4.24 (dd, J=11.1, 4.6 Hz, 1H), 4.10 ("t", J=9.1 Hz, 1H), 3.88 (dd, J=9.2, 6.0 Hz, 1H), 2.46 (s, 3H).

MS m/z (relative intensity) 365 (70.6,M$^+$), 149 (100), 122 (32.8), 91 (52.8).

HRMS m/z 365.0738 (calcd for $C_{17}H_{16}FNO_5S$: 365.0733).

Anal. calcd for $C_{17}H_{16}FNO_5S$: C, 55.88; H, 4.41; N, 3.83. Found: C, 55.96; H, 4.38; N, 3.80.

Preparation 11 (R)-[3-(3-fluorophenyl)-2-oxo-5-oxazolidinyl]methyl azide.

A solution of (R)-[3-(3-fluorophenyl)-2-oxo-5-oxazolidinyl]methyl-4-methylbenzene sulfonate (2.340 g, 6.40 mmol) in dry DMF (60 mL) was treated with solid sodium azide (3.331 g, 51.23 mmmol) at ambient temperature. The resultant slurry was warmed to 65° C. for 4.5 h and then cooled to ambient temperature and left overnight. The reaction mixture was then diluted with ethyl acetate and water, transferred to a separatory funnel, and extracted with ethyl acetate. The combined ethyl acetate extracts were washed thoroughly with water, and then dried ($Na_2SO_4$), filtered, and concentrated in vacuo to give the title compound as a white solid which was essentially pure. The following characteristics were noted:

mp 81°–82° C.

$[\alpha]^{25}_D$ −136.5° (c 0.9, $CHCl_3$).

IR (mineral oil mull) 2115, 1736, 1614, 1591, 1586, 1497, 1422, 1233, 1199, 1081, 1049 $cm^{-1}$.

$^1$H-NMR ($CDCl_3$, 300MHz)δ7.45 ("dt", J=11.2, 2.3 Hz, 1H), 7.34 ("dt", J=8.3, 6.4 Hz, 1H), 7.23 (ddd, J=8.1, 2.1, 1.0 Hz, 1H), 6.86 (dddd, J=8.2, 8.2, 2.5, 1.0 Hz, 1H), 4.81 (m, 1H), 4.09 ("t", J=8.9 Hz, 1H), 3.86 (dd, J=9.0, 6.2 Hz, 1H), 3.72 (dd, J=13.2, 4.5 Hz, 1H), 3.60 (dd, J=13.2, 4,4 Hz, 1H).

MS m/z (relative intensity) 236 (59.0,M$^{+)}$ 179 (94.9), 136 (59.5), 122 (62.4), 109 (71.8), 95 (100), 75 (40.7).

HRMS m/z 236.0708 (calcd for $C_{10}H_9FN_4O_2$: 236.0709).

Anal. calcd for $C_{10}H_9FN_4O_2$: C, 50.85; H, 3.84; N, 23.72. Found: C, 50.74; H, 3.76; N, 23.71.

Preparation 12 (S)-N-[[3-(3-fluorophenyl)-2-oxo-5-oxazolidinyl]methyl]acetamide.

A solution of (R)-[3-(3-fiourophenyl)-2-oxo-5-oxazolidinyl]methyl azide (8.200 g, 34.71 mmol) in ethyl acetate (100 mL) was treated with 10% palladium on carbon (0.820 g) under nitrogen. The atmosphere was then replaced with hydrogen (balloon) via repeated evacuation and filling. After stirring under hydrogen for 17 h, TLC (5% methanol/chloroform) revealed the azide to be consumed. The atmosphere was replaced with nitrogen and then pyridine (6 mL) and acetic anhydride (4.1 mL, 43.40 mmol) were added to the reaction mixture. The reaction mixture was stirred for 1 h at ambient temperature and then filtered through Celite, washing the pad with ethyl acetate. The filtrate was concentrated in vacuo and the residue taken-up in dichloromethane. The addition of diethyl ether afforded a precipitate. After standing in the refrigerator overnight the solids were collected by vacuum filtration, washed with cold hexane, and dried in vacuo to furnish 4.270 g of the title compound as a white solid. Another 3.700 g was obtained from the mother liquors for an overall yield of 91%. In another run, the crude product was purified by chromatography over silica gel, eluting with 5% methanol/chloroform. The following characteristics were noted:

mp 140.0°–140.5° C.

$[a]^{25}_D$ −6.6° (c 1.0, $CHCl_3$).

Preparation 13 (S)-N-[[3-(3-fluoro-4-iodophenyl)-2-oxo-5-oxazolidinyl]methyl]acetamide.

The (S)-N-[[3-(3-fluorophenyl)-2-oxo-5-oxazolidinyl] methyl]acetamide (0.280 g, 1.11 mmol) was dissolved in a mixture of acetic acid (20 mL) and trifluoroacetic acid (5 mL) and then treated with iodine monochloride (2.343 g, 14.43 mmol) at ambient temperature. The dark red-brown mixture was stirred at room temperature under nitrogen. An orange precipitate gradually formed. After ca. 24 h the reaction mixture was diluted with diethyl ether and the solids, collected by vacuum filtration through a medium-porosity sintered glass filter, washing with $Et_2O$. The crude solids were dissolved in hot chloroform (a little methanol was added to aid dissolution), transferred to a separatory funnel, and washed with saturated aqueous sodium bicarbonate, 20% aqueous sodium thiosulfate and brine. The organic phase was dried over sodium sulfate, filtered and concentrated in vacuo to afford 0.295 g (70%) of the title compound as a white solid. The following characteristics were noted:

mp 185.5°–186.5° C.

$[\alpha]^{25}_D$ −37.6° (c 1.0, DMF).

Preparation 14 (±)-5-Acetamidomethyl-3-(4'-trimethyltinphenyl)oxazolidin-2-one

A solution of hexamethylditin (1.772 g, 5.41 mmol) and (±)-5-acetamidomethyl- 3-(4'-iodophenyl)oxazolidin-2-one (1.840 g, 5.11 mmol) in 23 ml of dioxane was alternately evacuated and filled with nitrogen three times. Then bis-(triphenylphosphine)palladium(II) chloride (0.155 g, 0.22 mmol) was added and the system was again evacuated and filled with nitrogen three times and the system was heated at 96° C. overnight. The solvents were evaporated and the crude material was purified on a medium pressure silica column (40×63 µ2.5 cm×25 cm, packed with 1% methanol/chloroform, loaded with methylene chloride, and eluted with a gradient of methanol/chloroform) to give 1.148 g (56.5%) of the desired material as a white solid, mp 130°–132° C., along with 0.537 g (26.5%) of slightly less pure material.

1H NMR (CDCl$_3$, 300MHz) δ: 7.48 (s, 4H), 6.71 (bt, J=6.0 Hz, 1H), 4.77 (ddd, J=13.2 Hz, J'=8.7 Hz, J"=4.5 Hz, 1H), 4.05 (t, J=9.0 Hz, 1H), 3.80 (dd, J=9.0 Hz, J'=6.6 Hz, 1H), 3.63 (dd, J=6.0 Hz, J'4.5 Hz, 2H), 2.01 (s, 3H), 0.28 (t, J=27.0 Hz, 9H).

IR (mineral oil mull, cm$^{-1}$): 3356 (m), 1746 (s), 1665 (s).

Mass Spectrum: m/e (rel abundance): 398 (8.8,M$^+$), 383 (100), 382 (36.9), 381 (75.3), 380 (29.0), 379 (42.7), 43 (23.1), 29 (27.5); exact mass calc'd for $C_{15}H_{22}N_2O_3Sn$: 398.0650. Found: 398.662.

Analysis calc'd for $C_{15}H_{22}N_2O_3Sn$: C,45.37; H,5.58; N,7.06. Found C,45.28; H,5.51; N,6.87.

tLc: 5% Methanol\Chloroform: R$_f$=0.34.

Preparation 15 (R)-[3-[3,5-Difluorophenyl]-2-oxo-5-oxazolidinyl]methanol.

A solution of N-carbobenzyloxy-3,5-difluoroaniline (10.9 g, 30.01 mmol) in dry THF (250 mL) was cooled to –78° C. and then treated with the dropwise addition of n-BuLi (19.7 mL, 31.51 mmol) over 15 minutes. The reaction was allowed to stir at –78° C. for an hour before th dropwise treatment of (R)-(–)-glycidyl butyrate (4.67 mL, 33.01 mmol) over a 10 minute period. The reaction was stirred at –78° C. for two more hours before being allowed to slowly warm up to room temperature overnight (17 h). At this point, the reaction was diluted with EtOAc (300 mL) and then washed with both NH$_4$Cl (300 mL) and brine (300 mL). The organic layer was dried over anhydrous NaSO$_4$, filtered and then concentrated under reduced pressure to yield a golden oil. The oil was chromatographed on silica gel (250 g of SG, eluting with a gradient of 0–3% McOH in 10% CH$_3$CH/CHCl$_3$) to give 6.82 g (99%) of the title compound as a waxy, white solid with a mp 84–85° C. and a HRMS (M$^+$) calculated for $C_{10}H_9NO_3F_2$ 229.0550, found 229.0552.

Preparation 16 (R)-[[3-(3,5-difluorophenyl)-2-oxo5-oxazolidinyl]methyl]-p-toluensulfonate.

The (R)-[3-(3,5-Difluorophenyl)-2-oxo-5-oxazolidinyl] methanol (4.68 g, 20.42 mmol) was dissolved in puridine (35 mL) and then cooled to 0° c. (ice bath). The cold solution was next treated with p-toluenesulfonyl chloride (4.67 g, 24.50 mmol). The reaction was allowed to stir in the cole room overnight (17 h). The following morning, the produce was precipitated by quenching the reaction with ice water (100 mL). The material was isolated via suction filtration and then dried overnight unde high vacuum (20 h). The reaction yielded 7.46 g (95%) of the title compound as a white powdery solid with a mp 110.5°–111.5° C. and a HRMS (M$^{30}$) calculated for $C_{17}H_{15}NO_5F_2S$ 383.0639, found 383.0639.

Preparation 17 (R)-[[3-(3,5-difluorophenyl)-2-oxo5-oxazolindinyl]methyl]azide.

The (R)-[[3-(3,5-difluorophenyl)-2-oxo5-oxazolindinyl] methyl]-p-toluensulfonate (7.34 g, 19.15 mmol) was dissolved in dry DMF (50 mL) and then treated with solid NaN$_3$ (3.73 g, 57.44 mmol). The reaction was heated to 60° C. for 2.5 h and then allowed to cool to room temperature overnight (17 h). At this time, the reaction was found to be complete by TLC (6% CH$_3$CN/CHCl$_3$, UV short wave). The reaction was concentrated in vacuo to give an off-white solid. The crude product was dissolved in EtOAc (1 L) and then washed with water (400 mL). The aqueous portion was then back-extracted with more EtOAc (5×100 mL). The combined organic extracts were washed again with water (400 mL) and once with brine (400 mL). The organic portion was next dried over anhydrous Na$_2$SO$_4$, filtered and then concentrated under reduced pressure to give 4.45 g (91%) of the title compound as an off-white crystalline solid with mp 96.5°–98° C. and a HRMS (M$^+$) caluclated for $C_{10}H_8N_4O_2F_2$ 254.0615, found 254,0609.

Preparation 18 (S)-N-[[3-(3,5-difluorophenyl-2-oxo-5-oxazolidinyl]methyl]acetamide.

The (R)-[[3-(3,5-difluorophenyl)-2-oxo5-oxazolindinyl] methyl]azide (6.8 g, 26.75 mmol) was dissolved in dry THF (50 mL) and then treated with the portion-wise addition of triphenylphospine (10.52 g, 40.13 mmol) over a period of 30 min. After 2 h, the reaction was found to be complete by TLC (10% MeOH/CHCl$_3$, UV short wave). Next, the water (11.57 mL, 642 mmol) was added and the reaction was heated to 50° C. for 4 h. Upon cooling, the reaction was found to be incomplete by TLC (10% MeOH/CHCl$_3$, UV short wave), so more water (2.9 mL) was added. After and additional 4 h of heating (50° C.), the reaction was determined to be complete. The reaction was then diluted with CH$_2$Cl$_2$ (300 mL) and the product was extracted into 2N HCl (3×150 mL). The acidic layer was carefully neutralized by careful addition of 50 wt % NaOH to pH 14. The basified aqueous phase was then extracted with CH$_2$Cl$_2$ (3×150 mL). The combined organic phases were dried over anhydrous Na$_2$SO$_4$, filtered and concentrated under reduced pressure to give 4.53 g (74%) of a white crystalline solid. The crude amine (4.53 g) was dissolved in CH$_2$Cl$_2$ (100 mL) and pyridine (10 mL). The solution was cooled to 0° C. (ice bath) and then the acetic anhydride (5.05 mL, 53.5 mmol) was added dropwise via an additional funnel. The reaction was allowed to stir at room temperature overnight (20 h) under N$_2$. The following morning, the reaction was found to be complete by TLC (5% MeOH/CHCl$_3$, UV short wave). The reaction mixture was diluted with EtOAc (200 mL) and wash with 2N HCl (200 mL), saturated MaHCO$_3$ (200 mL), and brine (200 mL).

The organic layer was dried over anhydrous Na$_2$SO$_4$, filtered and then concentrated under reduced pressure to give 4.61 g (64% overall) of the title compound as a white solid with a melting point of 145°–148° C. and a HRMS (M$^+$) calculated for $C_{10}H_{12}N_2O_3F_2$ 270.0816, found 270.0815.

Preparation 19 (S)-N-[[3-(4-iodo-3,5-difluorophenyl)-2-oxo- 5-oxazolidinyl]methyl]acetamide.

The (S)-N-[[3-(3,5-difluorophenyl)-2-oxo-5-oxazolidinyl]methyl]acetamide (1.25 g, 4.64 mmol) was dissolved in glacial acetic acid (12 mL) and trifluoroacetic acid (3 mL) and then treated with solid I$_2$ (4.52 g, 27.84 mmol). The resultant deep purple solution was allowed to stir at room temperature overnight (20 h). An orange solid began to crash out of the solution almost immediately. The following morning, the reaction was diluted with ether (100 mL) and then filtered through a frit. The orange solid was rinsed with more ether (3×50 mL) and then dissolved in warm 10% MeOH/CHCl$_3$. The MeOH/CHCl$_3$ solution was washed with 20% Na$_2$S$_2$O$_3$ (100 mL), saturated NaHCO$_3$ (100 mL), and brine (100 mL). The organic portion was dried over anhydrous Na$_2$SO$_4$, filtered and concentrated under reduced pressure to yield 1.31 g (71%) of the title compound as an off-white solid with a melting point of 192°–193° C. and a HRMS (M$^+$) calculated for $C_{12}H_{11}N_2O_3F_2I$ 395.9784, found 395.9779.

Preparation 20 N-carbobenzyloxy-3,5-difluoroaniline.

The 3,5-difluoronitroaniline (10 g, 77.45 mmol) was added slowly to a slurry of NaHCO$_3$ (13.01 g, 154.9 mmol) in dry THF (200 mL). This solution was cooled to 0° C. (ice bath) and then treated dropwise with benzylchloroformate (22.11 mL, 154.9 mmol). Upon completion of the addition, the ice bath was removed and the reaction was allowed to stir under N$_2$ for 4 h. After this time, the reaction was determined to be complete by TLC (15% EtOAc/hexane, UV short wave). The reaction was quenched with saturated NaHCO$_3$ (300 mL) and extracted into CH$_2$Cl$_2$ (3×200 mL). The combined organic extracts were then washed with both water (400 mL) and brine (400 mL). The organic layer was next dried over anhydrous NaSO$_4$, filtered and concentrated under reduced pressure to yield a crystalline material coated with an amber oil. This material was chromatographed on silica gel (312 g of SG), eluting with 5 and 10% EtOAc/hexane to give 20.6 g (100%) of the title compound as a white solid with mp 86°–87° C. and MS (M$^+$) calculated for $C_{14}H_{11}F_2NO_2$ 263, found 263.

Preparation 21 N-allyl-N-carbobenzyloxy-3,5-difluoroaniline.

The N-carbobenzyloxy-3,5-difluoroaniline (10 g dissolved in minimum amount of THF, 37.99 mmol) was added dropwise to a precooled (0° C., ice bath) slurry of NaH (60% in oil, 2.28 g, 56.99 mmol) in dry THF (150 mL). Upon completion of the addition, the reaction was allowed to stir at 0° C. under N$_2$ for 30 min. At this point, both the catalyst, (n-Bu)$_4$NI (1.0 g, 10% by weight) and the allyl bromide (4.93 mL, 56.99 mmol) were added. The reaction was allowed to warm slowly to room temperature, stirring overnight under N$_2$ (17 h). The following morning, the reaction was found to be complete by TLC (15% EtOAc/hexane, UV short wave). The reaction mixture was quenched with water (150 mL) and then extracted into EtOAc (3×150 mL). The combined organic extracts were then washed with brine (400 mL) and dried over anhydrous Na$_2$SO$_4$. After drying, the solution was filtered and concentrated under reduced pressure to give a yellow oil. The oil was chromatographed on silica gel (250 g), eluting with 5 and 10% EtOAc/hexane to give 10.58 g (92%) of the title compound as a clear, colorless oil with MS (M$^+$) calculated for $C_{17}H_{15}F_2NO_2$ 303, found 303.

Preparation 22 (±)-[3-(3,5-difluorophenyl)-2-oxo-5-oxazolidinyl]iodomethane.

The N-allyl-N-carbobenzyloxy-3,5-difluoroaniline (11.5 g, 38.9 mmol) was dissolved in CHCl$_3$ (100 mL) and then treated with solid I$_2$ (19.37 g, 76.19 mmol). The resultant solution was allowed to stir at room temperature overnight (20 h) under N$_2$. The following morning, the reaction was found to be complete by TLC (15% EtOAc/hexane, UV short wave). The reaction mixture was diluted with CHCl$_3$ (200 mL) and washed with both 20% Na$_2$S$_2$O$_3$ (250 mL) and brine (250 mL). The organic layer was next dried over anhydrous N$_2$SO$_4$, filtered and concentrated to yield a golden oil. The oil was chromatographed on silica gel (300 g), eluting with both 15 and 50% EtOAc/hexane to give 12.67 g (98%) of the title compound as a cream colored solid with HRMS (M$^+$) calculated for $C_{10}H_8F_2INO_2$ 338.9570, found 338.9572.

Preparation 23 (±)-[[3-(3,5-difluorophenyl)-2-oxo-5-oxazolidinyl]methyl]azide. The (±)-[3-(3,5-difluorophenyl)-2-oxo-5-oxazolidinyl]iodomethane (12.64 g, 37.3 mmol) was dissolved in DMF (100 mL) and then treated with solid NaN$_3$ (7.28 g, 111.9 mmol). The resultant solution was heated to 60° C. for 2.5 h under N$_2$ and then allowed to return to room temperature, stirring overnight (16 h). The following morning, the reaction was found to be complete by TLC (6% CH$_3$CN/CHCl$_3$, UV short wave). The reaction mixture was quenched with water (1000 mL) and then extracted into EtOAc (3×150 mL). The combined organic extracts were washed again with water (400 mL) and once with brine (400 mL). The organic layer was next dried over anhydrous Na$_2$SO$_4$, filtered and concentrated under reduces pressure to yield 9.41 g (99%) of the title compound as a pale yellow solid with mp 72°–73° C. HRMS (M$^+$) calculated for $C_{10}H_8F_2N_4O_2$ 254.0615, found 254.0617.

Preparation 24 (±)-N-[[3-(3,5-difluorophenyl)-2-oxo-5-oxazolidinyl]methyl]acetamide.

The (±)-[[3-(3,5-difluorophenyl)-2-oxo-5-oxazolidinyl]methyl]azide (2.36 g, 9.30 mmol) was dissolved in 5% MeOH/EtOAc (200 mL) to give a clear yellow solution. This solution was degassed 3 times with N$_2$ and then treated with 10% Pd—C (460 mg, 20% by weight). The solution was degassed again (3×) and the atmosphere was replaced with H$_2$ via a balloon. The reaction stirred at room temperature for 20 h. After this time, the reaction was determined to be complete by TLC (30% EtOAc/hexane UV short wave). The reaction mixture was filtered through celite, washed the cake of celite with excess CH$_2$C$_{12}$. The filtrate was concentrated in vacuo to give a clear, colorless oil. This oil was redissolved in CH$_2$Cl$_2$ (20 mL) and pyridine (10 mL) and then treated with acetic anhydride (1.76 mL, 18.60 mmol). The reaction was allowed to stir overnight at room temperature under N$_2$ (17 h). In the morning, the reaction was diluted with EtOAc (100 mL) and washed with 2N HCl (2×100 mL), saturated NaHCO$_3$ (100 mL), and brine (100 mL). The organic layer was dried over anhydrous Na$_2$SO$_4$, filtered and concentrated under reduced pressure to yield a white solid. This solid was chromatographed on silica gel (175 g), eluting with a gradient of 0.5-2% MeOH in 10% CH$_3$CN/CHCl$_3$ to give 1.07 g (42%) of the title compound as a white solid with mp 131.5°–132.5° C. and HRMS (M$^+$) calculated for $C_{12}H_{12}F_2N_2O_3$ 270.0816, found 270.0810.

Preparation 25 (±)-N-[[3-(4-iodo-3,5-difluorophenyl)-2-oxo-5-oxazolidinyl]methyl]acetamide.

The (±)-N-[[3-(3,5-difluorophenyl)-2-oxo-5-oxazolidinyl]methyl]acetamide (500 mg, 1.85 mmol) was dissolved in acetic acid (5 mL) and then treated with IC$_1$ (1.8 g, 11.1 mmol). The resultant red-brown solution was allowed to stir overnight at room temperature (17 h). In the morning, the reaction was diluted with ether (50 mL) and then filtered through a glass flit. The residual orange solids were washed with more ether (3×30 mL) and then dissolved in warm 10% MeOH/CHCl$_3$ (100 mL). This solution was washed with 20% Na$_2$S$_2$O$_3$ (100 mL), saturated NaHCO$_3$ (100 mL), and brine (100 mL). After drying over anhydrous Na$_2$SO$_4$, the organic layer was filtered and then concentrated under reduced pressure to yield 387 mg of the title compound as a white solid. After 2 h, more product had crashed out of the filtrate. The solution was decanted and the remaining solids were washed with ether. Next, these solids were also dissolved in warm 10% MeOH/CHCl$_3$ (50 mL) and then washed with 20% Na$_2$S$_2$O$_3$ (50 mL), saturated NaHCO$_3$ (50 mL), and brine (50 mL). This organic layer was also dried over anhydrous Na$_2$SO$_4$, filtered and concentrated under reduced pressure to yield an additional 142 mg of the title compound as an off white solid. A total of 529 mg (72%) of the desired compound was isolated as a white solid with mp 191°–192° C. and HRMS (M$^+$) calculated for $C_{12}H_{11}F_2IN_2O_3$ 395.9784, found 395.9774.

Preparation 26 (±)-N-[[3-[4-(trimethylstannyl)-3,5-difluorophenyl]-2-oxo-5-oxazolidinyl]methyl]acetamide.

The (±)-N-[[3-(4-iodo-3,5-difluorophenyl)-2-oxo-5-oxazolidinyl]methyl]acetamide (100 mg, 0.25 mmol) was dissolved in 1,4-dioxane (15 mL) and then treated with the hexamethylditin (165 mg, 0.50 mmol). After the reaction mixture was degassed 3 times with $N_2$, the bis(triphenylphosphine)palladium(II) chloride (9 mg, 0.0125 mmol) was added. The solution was degassed again (3×) and heated to reflux (110° C.) for 5 h. After this time, the reaction was determined to be complete by TLC (10% MeOH/CHCl$_3$, UV short wave). The solvent was removed in vacuo, and the residual oil was chromatographed on silica gel (75 g), eluting with a gradient of 0.5–5% MeOH/CHCl$_3$ to give 105 mg (97%) of the title compound as a foamy, pale yellow solid with a HRMS (M$^+$) calculated for $C_{15}H_{20}N_2O_3F_2Sn$ 434.0461, found 434.0457.

EXAMPLE 1

(±)-Acetamide, N-[[3-[4 [(4-methoxy-5-oxo-1,3,6-cycloheptatrien- 1yl)phenyl]-2-oxo-5-oxazolidinyl]methyl]

The (±)-5-(Azidomethyl)-3-[4-(4-methoxy-5-oxo-1,3,6-cycloheptatrien-1-yl)phenyl- 2-oxazolidinone (100 mg, 0.286 mmol) was dissolved into a mixture of 10 ml of EtOAc and 4 ml of MeOH with the aid of sonication and gentle warming. The catalyst (10% Pd/C, 50 mg) was added under a stream of $N_2$. The flask was evacuated and flushed with $N_2$ (3 times) followed by introduction of $H_2$ via balloon. The mixture was stirred under $H_2$ at atmospheric pressure, and progress was monitored by TLC. After 3 hours TLC showed that 9 was consumed. The reaction mixture was filtered through a plug of celite and the filtrate was concentrated under reduced pressure. The oil was dissolved into 10 ml of $CH_2C_{12}$ and 1 ml of pyridine was added along with acetic anhydride (500 μL). After 10 minutes the reaction mixture was concentrated to a light yellow solid that was purified by radial chromatography (eluted with CHCl$_3$/MeOH mixtures, 1%–5%, 100 ml each). This gave 78 mg of the title compound, as a light yellow solid.

MP: 231°–232° C.

HRMS: calcd for $C_{20}H_{20}N_2O_5$: 368,1372. Found: 368.1364. $^1$H NMR: (CDCl$_3$): δ7.61 (d, 2H, J=8.8Hz), 7.53–7.51 (m, 1H), 7.515 (d, 2H, J=8.8 Hz), 7.34 (d, 1H, j=11.7 Hz), 7.31–7.28 (m, 1H), 6.97 (bt, 1H), 6.89 (d, 1H, J=11.7 Hz), 4.82 (m, 1H), 4.12 (t, 1H, J=9.1 Hz), 4.00 (s, 3H), 3.85 (dd, 1H, J+9.2 Hx), 3.67–3.65 (M, 2H), 2.03 (s, 3H).

EXAMPLE 2

(±)-Acetamide, N-[[3-[4[(4-methoxy-5-oxo-1,3,6-cycloheptatrien- 1-yl))phenyl]-2-oxo-5-oxazolidinyl]methyl]

The Trimethyl(4-methoxy-5-oxo-1,3,6-cycloheptatrien-1-yl)tin (50 mg, 0.167 mmol) was dissolved into 5 ml of 1,4-dioxane and the aryliodide (50mg, 0.139 mmol) was added. The mixture was degassed by evacuation and flushing with $N_2$ (3 times). Next the catalyst bis(triphenylphosphine)palladium dichloride (10 mg) was added and the mixture was degassed a final time. The mixture was heated to reflux under $N_2$ and progress was monitored by TLC. The mixture became homogeneous upon heating. After 5 hours TLC showed the starting material was consumed. The reaction mixture was cooled to ambient temperature followed by filtering the mixture through a plug of celite, which removed the Pd black from the mixture. The mother liquors were concentrated to give a solid residue which was purified by radial chromatography. The silica was eluted with CHCl$_3$/MeOH mixtures (1% to 5%) in 100 ml portions. The fractions corresponding by TLC to an authentic sample of 10 were collected and concentrated to give a yellow foam. The foam was dissolved into a minimal volume of $CH_2C_{12}$ and a solid was precipitated by the addition of ether. The solid was filtered, washed with ether and dried in vacuo to give 37mg of the title compound. This material was identical in all respects to an authentic sample by comparison of the TLC, $^1$H NMR and top.

EXAMPLE 3

(±)-Acetamide, N-[[3-[3-fluoro-4-(4-methoxy-5-oxo-1,3,6-cycloheptatrien- 1-yl)phenyl]-2-oxo-5-oxazolidinyl]methyl]

The aryliodide 19 (50 mg, 0.132 mmol) was dissolved into 4 ml of 1,4-dioxane and the tropylstannane 11 (43.5mg, 0.146 mmol) was added. The mixture was degassed by evacuation and flushing with $N_2$ (3 times) and the catalyst Pd(Ph$_3$P)$_2$CL$_2$ (9.3 mg) was added. The mixture was degassed a final time followed by heating to reflux. Progress was monitered by TLC. After 8 hours TLC showed 19 was essentially consumed. The mixture was concentrated to a brown solid that was dissolved into 10% MeOH/CHCl$_3$ and filtered through a small plug of silica gel. The filtrate was concentrated to a solid that was purified by radial chromatography eluting with CHCl$_3$/MeOH mixtures (1% MeOH moving to 6% in 75 ml volumes). Isolated 40mg of the title compound 20 as an off white solid.

MP: 200°–201° C.

Anal. Calcd for $C_{20}H_{19}FN_2O_5$: C, 62.17; H, 4.96: N, 7.25. Found: C, 60.62; H, 4.99: N, 6.98

HRMS: Calcd for $C_{20}H_{19}FN_2O_5$: 388.1278: Found 386.1271 hu 1H NMR (CDCl$_3$): δ7.55 (d, 1H), 7.42–7.31 (m, 4H), 7.205 (d, 1H, J=10.5 Hz), 682 (d, 1H, J=10.5 Hz), 6.10 (bt, 1H), 4.82 (m, 1H), 4.09 (t, 1H, J=9.00 Hz), 4.00 (s, 3H), 3.85 (m, 1H), 3.70 (m, 2H), 2.04 (s, 3H).

The following is a representative procedure for the amine displacement reactions of the methoxy-substituted examples of formula Ia–c.

EXAMPLE 4

(±)-Acetamide, N-[[2-oxo-3-[4-[5-oxo-4-[(phenylmethyl)amino]- 1,3,6-cycloheptatrien-1-yl]phenyl]-5-oxazolidinyl]methyl]

(±)-Acetamide, N-[[3-[4[(4-methoxy-5-oxo-1,3,6-cycloheptatrien-1-yl)phenyl]- 2-oxo-5-oxazolidinyl]methyl](25 mg, 0.07 mmol) was slurried into a mixture of 1.5 ml of benzyl amine and 5 ml of dry toluene. The mixture was heated to a gentle reflux under $N_2$. After 16 hours the mixture showed 10 was consumed by TLC. The mixture was cooled to ambient temperature and diluted with 15 ml of ether. The precipitates were filtered and washed with ether. The bright yellow solids were dried in vacuo. This gave 32 mg of the title compound.

MP: 239°–240° C.

Anal. Calcd for $C_{26}H_{25}N_3O_4$: C, 70.41; H, 5.68: N, 9.47. Found: C, 70.06; H, 5.67; N, 9.41.

HRMS: Calcd for $C_{26}H_{25}N_3O_4$: 443.1845: Found 443.1859.

$^1$H NMR (CDCl$_3$): δ7.66–7.54 (m, 3H), 7.465 (d, 1H), 7.48–7.32 (m, 7H), 7.27 (d, 1H, J=11.5 Hz), 6.70 (d, 1H, J=11.5 Hz), 4.80 (m, 1H), 4.63 (s, 2H), 4.12 (T, 1H, J=9.1 Hz), 3.85–3.80 (m, 1H), 3.65–3.59 (m, 2H), 2.02 (s, 3H).

Utilizing a procedure similar to that used in Example 4 but substituting the appropriate amine for benzyl amine the following compounds are obtained:

(±)-Acetamide, N-[[2-oxo-3-[4-[5-oxo-4-[(diethyl)amino]-1,3,6-cycloheptatrien- 2yl]phenyl]-5-oxazolidinyl]methyl]

MP: 164°–165° C.

Calcd for $C_{23}H_{27}N_3O_4$: 409.2001: Found 409.1994.

$^1$H NMR (CDCl$_3$): δ7.57–7.46 (m, 3H), 7.37–7.24 (m, 3H), 6.97 (d, 1H, J=12.2 Hz), 6.655 (d, 1H, J=11.2 Hz), 4.82 (m, 1H), 4.12 (t, 1H, J=9.0 Hz), 3.88–3.83 (m, 1H)

(±)-Acetamide, N-[[2-oxo-3-[[4-[5-oxo-4-[(2-hydroxyethyl)amino]- 1,3,6-cycloheptatrien-1-yl]phenyl]-5-oxazoldinyl]methyl

MP: 212°–213° C.

HRMS: Calcd for: $C_{21}H_{23}N_3O_5$: +H$_1$: 398.1716: Found 398.1735

$^1$H NMR (CDCl$_3$): δ7.56–7.43 (m, 6H), 7.20 (d, 1H, J=11.5 Hz), 4.78–4.87 (m,1H), 4.10 (t, 1H, J=9.0 Hz), 3.94 (bt, 2H), 3.86–3.84 (m, 1H), 3.66 (bt, 2H), 3.53 (bt, 2H), 2.03 (s, 3H).

(±)-Acetamide, N-[[2-oxo-3-[4-[5-oxo-(4-morpholinyl)- 1,3,6-cycloheptatrien- 1-yl]phenyl]-5-oxazolidinyl]methyl]

MP: 231°–232° C.

HRMS: Calcd for: $C_{23}H_{25}N_3O_5$: 423.1794: Found 423.1785

$^1$H NMR (CDCl$_3$): δ7.585 (d, 2H, J=8.8 Hz), 7.485 (d, 2H, J=8.8 Hz), 7.38 (dd, 1H, J=12.5 Hz), 7.225 (dd, 1H, J=10.7 Hz), 7.12 (d, 1H, J=12.5 Hz), 6.775 (d, 1H, J=0.7 Hz), 6.11 (bt, 1H), 4.81 (m, 1H), 4.10 (t, 1H, J=9.1 Hz), 3.90 (bt, 4 H, J=4.6 Hz), 3.835 (dd, 1H, J=9.1 Hz), 3.70–3.67 (m, 2H), 3.39 (bt, 4H, J=4.6 Hz), 2.04 (s, 3H).

(±)-Acetamide, N-[[2-oxo-3-[4-[5-oxo-4-[(cyclopropylamino]-1,3,6-cycloheptatrien- 1-yl]phenyl]-5-oxazolidinyl]methyl]

MP: 233°–234° C.

MS(EI): m/z (rel int.) 393[M+](68), 337(31), 222(30), 181(34), 42(100).

$^1$H NMR (CDCl$_3$): δ7.88–7.48 (m, 6H), 7.195 (d, 1H, J=12.1 Hz), 7.125 (d, 1H, J=10.8 Hz), 4.81 (m, 1H), 4.10 (t, 1H, J=9.0 Hz), 3.875 (dd, 1H, J=9.0 Hz), 3.64 (bt, 2H, J-5.5 Hz), 2.65–2.62 (m, 1H), 2.01 (s, 3H), 1.01–0.95 (m, 2H), 0.73–0.68 (m, 2H).

(±-Acetamide, N-[[2-oxo-3-[4-[5-oxo-4-[(4-carboxaldehyde)piperazinyl]- 1,3,6-cycloheptatrien-1-yl]phenyl]-5-oxazolidinyl]]methyl]

MP: 255°–257° dec.

MS(EI): m/z (rel. int.) 450[M+](5), 406(86), 56(100).

$^1$H NMR (CDCl$_3$): δ7.61–7.57 (m, 2H), 7.51-7.42 (m, 3H), 7.28–7.23 (m, 1H), 7.18 (d, 1H, J=12.5 Hz), 6.82 (d, 1H, J=10.7 Hz), 6.73 (bt, 1H), 4.80 (m, 1H), 4.11 (t, 1H, J=9.0 Hz), 3.84–3.78 (m, 2H), 3.70–3.60 (m, 4H), 3.40 (bt, 3H), 3.32 (bt, 1H), 3.09 (bt, 1H), 2.03 (s, 3H).

(±-Acetamide, N-[[2-oxo-3-[4-[5-oxo-4-[(2-propenyl)amino ]- 1,3,6-cycloheptatrien-1-yl ]-5-oxazolidinyl]methyl]

MP: 213°–215° C.

HRMS: Calcd for: $C_{22}H_{23}N_3O_4$: 393.1688: Found 393.1673.

$^1$H NMR (CDCl$_3$): δ7.62–7.43 (m, 6H), 7.255 (d, 1H, J=12.1 Hz), 6.645 (d, 1H, J=11.0 Hz), 6.00–6.63 (m, 1H), 5.29–5.26 (m, 1H), 4.81 (m, 1H), 4.11 (t, 1H, J=9.0 Hz), 4.06 (m, 2H), 3.87–3.81 (m, 1H), 3.68–3.66 (m, 2H), 2.03 (s, 3H).

(±)-Acetamide, N-[[2-oxo-3-[4-[5-oxo-4-[pyrrolidin-1-yl]- 1,3,6-cycloheptatrien-1-yl]phenyl]-5-oxazolidinyl]methyl]

MP: 230–231

HRMS: $C_{23}H_{25}N_3O_4$: 407.1845: Found 407.1859

$^1$H NMR (CDCl$^3$): δ7.555 (d, 2H, J=8.9 Hz), 7.455 (d, 2H, J=8.9 Hz), 7.345 (dd, 1H, J=10.1 Hz), 7.26 (dd, 1H, J=11.3 Hz), 6.98 (d, 1H, J=12.1 Hz), 6.78 (bt, 1H), 6.445 (d, 1H, J=11.2 Hz), 4.79 (m, 1H), 4.10 (t, 1H, J=9.0 Hz), 3.825 (dd, 1H, J=9.0 Hz), 3.69 (bs, 6H), 2.03 (s, 3H), 1.98 (bs, 4H).

(±)-Acetamide, N-[[2-oxo-3-[4-[5-oxo-4-(4-methylpiperazin-1-yl)- 1,3,6-cycloheptatrien-1-yl]phenyl]-5-oxazolidinyl]methyl]

MP: 204°–206° C.

HRMS: Calcd For: $C_{24}H_{28}N_4O_4$: 436.2110: Found 436.2117

$^1$H NMR (CDCl$_3$): δ7.575 (d, 2H, J=8.8 Hz), 7.475 (d, 2H, J=8.8 Hz), 7.375 (dd, 1H, J=12.5 Hz), 7.255 (dd, 1H, J=10.7 Hz), 7.10 (d, 1H, J=12.5 Hz), 6.80 (d, 1 H J-10.7 Hz), 6.17 (bt, 1H), 4.81 (m, 1H), 4.10 (t, 1H, J=9.0 Hz), 3.835 (dd, 1H, J=9.0 Hz), 3.72–3.61 (m, 2H), 3.43 (bt, 4H, J=4.80 Hz), 2.62 (bt, 4H, J=4.80 Hz), 2.36 (s, 3H), 2.04 (s, 3H).

(±)-Acetamide, N-[[2-oxo-3-[4-[5-oxo-4-[(cyclopentyl)amino]-1,3,6-cycloheptatrien- 1-yl]phenyl]-5-oxazolidinyl]methyl]

MP: 208°–210° C.

HRMS: Calcd for: $C_{24}H_{27}N_3O_4$: 421.2001: Found 421.1987

$^1$H NMR (CDCl$_3$): δ7.61–7.44 (m, 6H), 7.20 (d, 1H, J=12.0 Hz), 6.71 (d, 1H, J=112 Hz), 4.81 (m, 1H), 4.10 (t, 1H, J=9.0 Hz), 4.00 (m, 1H), 3.865 (dd, 1H, J=10.0 Hz), 3.68–3.66 (m, 2H), 2.20–2.10 (m, 2H), 2.04 (s, 3H), 1.81-1.68 (m, 6H).

(±)-Acetamide, N-[[2-oxo-3-[4-[5-oxo-4-[piperazin-1-yl] -1,3,6-cycloheptatrien- 1-yl]phenyl]-5-oxazolidinyl]methyl]

MP: >300° C.

HRMS: Calcd for: $C_{23}H_{26}N_4O_4$: 422.1954: Found 422.1964

$^1$H NMR (CDCl$_3$): δ7.585 (d, 2H, J=8.8 Hz), 7.485 (d, 2H, J=8.8 Hz), 7.395 (dd, 1H, (J=12.5 Hz), 7.255 (dd, 1H, J=10.8 Hz), 7.12 (d, 1H, J=12.5 Hz), 6.815 (d, 1H, J=10.8 Hz), 6.70 (bt, 1H), 4.81 (m, 1H), 4.11 (t, 1H, J-9.0 Hz), 3.854 (dd, 1H, J-8.8 Hz), 3.68 (m, 2H), 3.38 (bt, 4H, J=4.8 Hz), 3.08 (bt, 4H, J=4.8 Hz), 2.03 (s, 3H).

(±)-Acetamide, N-[[2-oxo-3-[4-[5-oxo-4-[(n-butyl)amino]-1,3,6-cycloheptatrien- 1-yl]phenyl]-5-oxazolidinyl]methyl]

MP: 197°–198° C.

HRMS:

$^1$H NMR (CDCl$_3$): δ7.58–7.45 (m, 6H), 7.22 (d, 1H, J=12.0 Hz), 6.66 (d, 1H, J=11.0 Hz), 4.80 (m, 1H), 4.11 (t, 1H, J=9.0 Hz), 3.835 (dd, 1H, J=9.1 Hz), 3.68 (m, 2H), 3.36 (t, 2H, J=7.2 Hz), 2.03 (s, 3H), 1.78–1.74 (m, 2H), 1.53–1.45 (m, 2H), 100 (t, 3H, J=7.2 Hz).

(±)-Acetamide, N-[[2-oxo-3-[4-[5-oxo-4-(cis-3,5-dimethylpiperazin-1-yl) 1,3,6-cycloheptatrien-1-yl]-2-oxo-5-oxazolidinyl]methyl]

MP: 142°–144° C.

MS(EI): m/z(rel. int.) 450[M+](45), 380(54), 366(43), 367(53), 84(100).

$^1$H NMR (CDCl$_3$): δ7.585 (d, 2H, J=8.8 Hz), 7.475 (d, 2H, J=8.8 Hz), 7.355 (dd, 1H, J=12.5 Hz), 7.215 (dd, 1H, J=10.8 Hz), 7.10 (d, 1H, J=12.5 Hz), 6.79 (d, 1H, J=10.8 Hz), 6.12 (bt, 1H), 4.80 (m, 1H), 4.11 (t, 1H, J=9.0 Hz), 3.89–3.81 (m, 3H), 3.49–3.47 (m, 2H), 3.16 (m, 2H), 2.45 (bt, 2H, J=112.4 Hz), 2.04 (s, 3H), 1.18 (d, 6H, J=6.30 Hz).

(±)-Acetamide, N-[[2-oxo-3-[4-[5-oxo-4-[piperidin-1-yl] -1,3,6-cycloheptatrien- 1-yl]phenyl]-5-oxazolidinyl]methyl]

MP: 211°–212° C.

HRMS: Calcd for: $C_{24}H_{27}N_3O_4$: 421.2001: Found 421.2007

$^1$H NMR (CDCl$_3$): δ7.565 (d, 2H, J=8.8 Hz), 7.465 (d, 2H, J=8.8 Hz), 7.33 (dd, 1H, J=12.4 Hz), 7.195 (dd, 1H, J=10.8 Hz), 7.07 (d, 1H, J=12.4 Hz), 6.80 (d, 1H, J=10.8

Hz), 6.25 (bt, 1H), 4.81 (m, 1H), 4.10 (t, 1H, J=9.0 Hz), 3.835 (dd, 1H, J=9.0 Hz), 3.72–3.61 (m, 2H), 3.41–3.39 (m, 4H), 2.04 (s, 3H), 1.74–1.72 (m, 6H).

(±)-Acetamide, N-[[2-oxo-3-[-[5-oxo-4-(3-methylpiperazin-1-yl)- 1,3,6-cycloheptatrien-1-yl]phenyl]-5-oxazolidinyl]methyl]

MP: 189°–191° C.

HRMS: Calcd for: $C_{24}H_{28}N_4O_4$: 436.2110: Found 436.2110

$^1$H NMR (CDCl$_3$): δ7.575 (d, 2H, J=8.8 Hz), 7.485 (d, 2H, J=8.8 Hz), 7.395 (d, 1H, J=12.5 Hz), 7.255 (dd, 1H J=10.7 Hz), 7.255 (dd, 1H, J=10.7 Hz), 7.12 (d, 1H, J=12.4 Hz), 6.82 (d, 1H, J=10.7 Hz), 4.81 (m, 1H), 4.11 (t, 1H, J=9.0 Hz), 3.86–3.83 (m, 3H), 3.67–3.63 (m, 2H), 2.87 (m, 1H), 2.50 (bt, 1H, J=10.4 Hz), 2.03 (s, 3H), 1.14 (d, 3H, J=6.3 Hz).

(±)-Acetamide, N-[[2-oxo-3-[4-[5-oxo-4-(3-hydroxypyrolidin-1-yl- 1,3,6-cycloheptatrien-1-yl]-phenyl]-5-oxazolidinyl]methyl]

MP: 223°–224° C.

HRMS: Calcd for: $C_{23}H_{25}N_3O_5+H_1$: 424.1872: Found 424.1900

$^1$H NMR (CDCl$_3$): δ7.495 (d, 2H, J=8.8 Hz), 7.395 (d, 2H, J=8.8 Hz), 7.32 (d, 1H, J-12.2 Hz), 7.23 (d, 1H, J=11.2 Hz), 6.95 (d, 1H, J=12.2 Hz), 6.465 (d, 1H, J=11.2 Hz), 4.81 (m, 1H), 4.56 (m, 1H), 4.09 (t, 1H, J-9.0 Hz), 3.99–3.95 (bd, 1H), 3.85–3.77 (m, 3H), 3.67–3.66 (m, 2H), 2.93–2.88 (m, 1H), 2.07 (bs, 2H), 2.03 (s, 3H).

EXAMPLE 5

(±)-N-[[3-[4-(4-ethoxy-5-oxo-1,3,6-cycloheptatrien-1-yl)phenyl]- 2-oxo-5-oxazolidinyl]methyl]acetamide A slurry of (±)-N-[[3-[4-(4-methoxy-5-oxo-1,3,6-cycloheptatrien-1-yl)phenyl]- 2-oxo-5-oxazolidinyl]methyl]acetamide (0.100 g, 0.27 mmol) in absolute ethanol (10 mL) was treated with a catalytic quantity of sodium hydride (5 mg of a 60% dispersion in mineral oil). The mixture was heated to reflux under nitrogen, during which time the mixture became a homogeneous solution. After 15 min of reflux the solution was cooled to ambient temperature and a solid precipitate noted. The reaction mixture was diluted with diethyl ether and the solids collected by filtration. After drying in vacuo, 0.088 g (85%) of the title compound was obtained as a light yellow solid with the following characteristics:

mp 228°–229° C.

$^1$H-NMR (CDCl$_3$, 300MHz) δ7.60 (d, J=8.7 Hz, 2H), 7.52–7.47 (m, 1H), 7.48 (d, J=8.5 Hz, 2H), 7.33–7.26 (m, 1H), 7.24 (d, J=10.5 Hz, 1H), 6.87 (d, J=10.6 Hz, 1H), 6.80 (bt, 1H), 4.82 (m, 1H), 4.19 (q, J=6.9 Hz, 2H), 4.11 ("t", J=8.9 Hz, 1H), 3.86 (dd, J=9.0, 6.8 Hz, 1H), 3.75–3.60 (m, 2H), 2.03 (s, 3H), 1.56 (t, J=6.9 Hz, 3H).

MS m/z (relative intensity) 382 (36.5,M+), 338 (55.0), 310 (26.3), 254 (26.8), 226 (100.0).

HRMS m/z 382.1536 (calcd for $C_{21}H_{22}N_2O_5$: 382.1529).

EXAMPLE 6

(S)-N-[[3-[3-fluoro-4-(4-methoxy-5-oxo-1,3,6-cycloheptatrien- 1-yl)phenyl]-2-oxo-5-oxazolidinyl]methyl]acetamide A slurry of (S)-N-[[3-(3-fluoro-4-iodophenyl)-2-oxo-5-oxazolidinyl]methyl]acetamide described above (4.200 g, 11.11 mmol) and trimethyl(4-methoxy-5-oxo-1,3,6-cycloheptatrien-1-yl)tin (4.150 g, 13.88 mmol) in 1,4-dioxane (50 mL) was degassed by repeated evacuation and filling with nitrogen. Bis(triphenylphosphine)palladium(II) chloride (0.545 g, 0.78 mmol) was added, the reaction again degassed, and then the mixture was brought to reflux under nitrogen. After 3 h TLC revealed some of the iodide still remained. Additional tin reagent (0.400 g, 1.34 mmol) and palladium catalyst (0.100 g, 0.14 mmol) were added and the mixture refluxed for 4 h. The reaction mixture was cooled to ambient temperature and concentrated under reduced pressure. The residue was dissolved in 20% methanol/chloroform, filtered through Celite and concentrated in vacuo. The crude solids were triturated with dichloromethane/diethyl ether, the solids filtered, washed with diethyl ether and dried in vacuo to give 4.200 g (98%) of the title compound. The following characteristics were noted:

mp 227°–228° C.

$[α]^{25}_D$+39.5° (c 0.9, DMF).

Alternatively, the oxazolidinone iodide described above can be converted to (S)-N-[[3-[3-fluoro-4-(trimethylstannyl)phenyl]-2-oxo-5-oxazolidinyl]methyl]acetamide, employing conditions disclosed for the corresponding racemic material in TR 7246- 92-050. This tin-substituted intermediate (0.180 g, 0.43 mmol) and 5-bromo- 2-methoxycyclohepta-2,4,6-trien-1-one (0.103 g, 0.48 mmol) were dissolved in dry DMF (3 mL) and the resultant solution degassed by repeated evacuation and filling with nitrogen. Bis(triphenylphosphine)palladium(II) chloride (0.015 g, 0.02 mmol) was added, the reaction again degassed, and the mixture heated to 80° C. for 2 h. TLC revealed some starting material still remained, so additional palladium catalyst (0.015 g) was added and the mixture heated a further 5 h. The reaction mixture was concentrated in vacuo and the residue chromatographed over silica gel, eluting with a methanol/chloroform gradient, to afford 0.096 g (57%) of the title compound, identical in all respects to material prepared via the above protocol.

EXAMPLE 7

(±)-N-[[3-[4-(4-methoxy-3-oxo-1,4,6-cycloheptatrien-1-yl)phenyl]- 2-oxo-5-oxazolidinyl]methyl]acetamide A dioxane (50 ml) solution of the (±)-5-acetamidomethyl-3-( 4'-trimethyltinphenyl)oxazolidin-2-one (1.172 g, 2.95 mmol) and 6-bromo- 2-methoxycyclohepta-2,4,6-trien-1-one (0.677 g, 3.13 mmol) was alternately evacuated and filled with nitrogen three times. Then bis(triphenylphosphine)palladium(II) chloride (0.200 g, 0.28 mmol) was added. The system was again evacuated and filled with nitrogen three times and was heated overnight at 90 ° C. Reaction was not complete; therefore 0.103 g (0.15 mmol) of palladium catalyst was added, the system was alternately evacuated and filled with nitrogen four times. After refluxing for two hours, the mixture was filtered through a plug of diatomaceous earth which was washed carefully with methylene chloride and methanol. The solvents were evaporated to give crude material which was purified on a medium pressure silica column (40×63 μ, 2.5 cm×26 cm, packed with 1% methanol/chloroform, loaded with chloroform, and eluted with a gradient of methanol/chloroform) to give 0.889 g (82% yield) of the desired material as a white solid. This material was then recrystallized from acetone to give 0.557 g (51.2%) of white solid, mp 213°–214° C. for analysis.

$^1$H NMR (CDCl$_3$, 300MHz) δ: 7.63 (d, J=9.0 Hz, 2H), 7.60 (d, J=9.0 Hz, 2H), 7.45 (s, 1H), 7.10 (m, 2H), 6.73 (d, J=8.7 Hz, 1H), 6.02 (bt, J=6.0 Hz, 1H), 4.81 (m, 8 lines, 1H), 4.12 (t, J=9.0 Hz, 1H), 3.98 (s, 3H), 3.78 (dd, J=9.0 Hz, J"=6.9 Hz, 1H), 3.74 (ddd, J=14.7 Hz, J'=6.0 Hz, J"=3.3 Hz, 1H), 3.64 (dt, J=14.7 Hz, J'=6.0 Hz, 1H), 2.04 (s, 3H).

$^{13}$C NMR (75.47MHz, CDCl$_3$): 23.11, 41.93, 47.46, 56.34, 72.00, 111.63, 118.25, 128.62, 129.52, 132.17, 135.72, 137.97, 138.75, 148.91, 154.38, 165.16, 170.63, 179.38.

IR (mineral oil mull, cm$^{-1}$): 3307 (m), 1739 (s), 1649 (m), 1592 (s), 1575 (s), 1561 (s).

Mass Spectrum: m/e (rel. abundance): 368 (9.8,M$^+$), 340 (32.3), 296 (24.1), 240 (26.5), 237 (20.5), 212 (100), 199 (34.3), 85 (37.6), 56 (28.2), 43 (29.5), 29 (34.1); exact mass calc'd for $C_{20}H_{20}N_2O_5$: 368.1372. Found: 368.1385.

Analysis calc'd for $C_{20}H_{20}N_2O_5$: C, 65.21; H, 5.47; N, 7.60. Found: C, 64.79; H, 5.28; N, 7.60.

TLC: 5%methanol/Chloroform: $R_f$=0.21.

EXAMPLE 8

(-±)-N-[[3-[4-(6-methoxy-5-oxo-1,3,6-cycloheptatrien-1-yl)phenyl]- 2-oxo-5-oxazolidinyl]methyl]acetamide, Ic A acetonitrile (25 ml) solution of (±)-5-acetamidomethyl-3-( 4'-trimethyltinphenyl)oxazolidin-2-one (0.352 g, 0.89 mmol) and 4-bromo- 2-methoxycyclohepta-2,4,6-trien-1-one (0.200 g, 0.93 mmol) was alternately evacuated and filled with nitrogen three times. Then bis(triphenylphosphine)palladium(II) chloride (0.076 g, 0.11 mmol) was added and the system was again evacuated and filled with nitrogen three times. The mixture was refluxed overnight, then was filtered through a plug of diatomaceous earth which was washed carefully with methylene chloride. The solvents were evaporated to give crude material which was purified on a medium pressure silica column (40×63 µ2.5 cm×27 cm, packed with 1% methanol/chloroform, loaded with chloroform, and eluted with a gradient of methanol/chloroform) to give 0.277 g (85%) of the desired material as a yellow solid. This material was recrystallized from acetone and water to give 0.123 g (38%) of yellow solid, mp 107°–110° C.

$^1$H NMR (CDCl$_3$, 300MHz) δ:7.63 (d, J=9.0 Hz, 2H), 7.56 (d, J=9.0 Hz, 2H), 7.31 (m, 1H), 7.20 (dd, J=12.0 Hz, J'=0.9 Hz, 1H), 7.02 (dd, J=7.5 Hz, J'=0.9 Hz, 1H), 6.94 (s, 1H), 6.07 (t, J=6.0 Hz, 1H), 4.83 (m, 9 lines, 1H), 4.13 (t, J=9.0 Hz, 1H), 3.99 (s, 3H), 3.87 (dd, J=9.0 Hz, J'=6.9 Hz, 1H), 3.74 (ddd, J=14.7 Hz, J'=6.3 Hz, J"=3.6 Hz, 1H), 3.66 (dt, J=14.7 Hz, J'=6.0 Hz, 1H), 2.04 (s, 3H).

$^{13}$C NMR (75.47MHz, CDCl$_3$): 23.12, 41.96, 47.55, 56.37, 72.09, 114.39, 118.55, 126.87, 128.39, 135.41, 136.52, 138.13, 139.06, 145.78, 154.22, 164.53, 171.09, 179.84.

IR (mineral oil mull, cm$^{-1}$): 3469 (br), 3288 (br), 1745 (s), 1662 (m).

Mass Spectrum: m/e (rel. abundance): 368 (72.4,M$^+$), 296 (33.3), 237 (35.9), 236 (34.3), 212 (100), 199 (56.8), 85 (53.8), 56 (49.8), 44 (30.3), 43 (50.1); exact mass calc'd for $C_{20}H_{20}N_2O_5$: 368.1372. Found: 368.1384.

Analysis calc'd for $C_{20}H_{20}N_2O_5$: C, 65.21; H, 5.47; N, 7.60. Found: C, 62.05; H, 5.74; N, 7.09.

TLC: 5%Methanol/Chloroform: $R_f$=0.17.

EXAMPLE 9

(±)-N-[[3-[4-[4-(2-propenyl)amino-3-oxo-1,4,6-cycloheptatrien- 1yl]phjenyl]-2-oxo-5-oxo-5-oxazolidinyl]methyl]acetamide (Ib)

A solution of methoxytropone-substituted oxazolidinone (0.077 g, 0.21 mmol) and allyl amine (3.5 ml, 46.6 mmol) was refluxed under nitrogen atmosphere overnight. The reaction mixture was then concentrated in vacuo to give crude material which was purified on a 1000 µ preparative TLC plate (eluted three times with 3% methanol/methylene chloride) to give the desired compound in quantitative yield as a yellow solid. This material was further purified on another preparative TLC plate (250 µ, eluted with 75% acetone/methylene chloride three times) to give 0.033 g (40%) of the title compound as a yellow solid, mp 169°–171 ° C., along with 0.026 g (32%) of slightly less pure material.

$^1$H NMR (CDCl$_3$, 300MHz) δ: 7.59 (bs, 4H), 7.47 (bt, J=6.0 Hz, 1H), 7.40 (d, J =1.8 Hz, 1H), 7.25 (t, J=10.5, 1H), 6.88 (dd, J=10.5 Hz, J'=1.8 Hz, 1H), 6.51 (d, J =10.5 Hz, 1H), 6.13 (bt, J=6.0 Hz, 1H), 5.94 (m, 10 lines, 1H), 5.29 (m, 2H), 4.81 (m, 9 lines, 1H), 4.12 (t, J=9.0 Hz, 1H), 4.03 (t, J=5.7 Hz, 2H), 3.84 (dd, J=9.3 Hz, J'=6.9 Hz, 1H), 3.73 (ddd, J=14.7 Hz, J'=6.0 Hz, J"=3.3 Hz, 1H), 3.64 (dt, J =14.7 Hz, J'=6.0 Hz, 1H), 2.04 (s, 3H).

$^{13}$C NMR (75.47MHz, CDCl$_3$): 0.01, 23.13, 41.88, 45.15, 47.53, 71.95, 108.21, 117.57, 118.23, 123.59, 128.78, 132.05, 135.46, 137.81, 139.38, 149.38, 154.06, 155.16, 170.63, 175.16.

IR (mineral oil mull, cm$^{-1}$): 3348 (m), 3293 (m), 1745 (s), 1662 (s), 1589 (s).

Mass Spectrum: m/e (rel. abundance): 393 (100,M$^+$), 394 (24.7), 265 (18.7), 152 (11.0), 56 (33.0), 44 (14.6), 43 (22.9), 29 (31.3); exact mass calc'd for $C_{22}H$ 393.1688. Found: 393.1685.

Analysis calc'd for $C_{22}H_{23}N_3O_4$: C, 67.16; H, 5.89; N, 10.68. Found: C, 64.74; H, 5.74; N, 9.83.

TLC: 2.5% Methanol/Chloroform×2: $R_f$=0.36.

EXAMPLE 10

(±)-N-[[3-[4-[4-(4-morpholinyl)-3-oxo-1,4,6-cycloheptatrien- 1yl]phenyl]-2-oxo-5-oxazolidinyl]methyl]acetamide (Ib)

A solution of the methoxytropone-substituted oxazolidinone (0.078 g, 0.21 mmol) and morpholine (0.3 ml, 3.43 mmol) in 3.5 ml of toluene was refluxed overnight. The solvents were evaporated and the crude material was purified on a preparative TLC plate (1000 µ, eluted with 3% methanol/methylene chloride two times) to give a quantitative yield of the desired material as a yellow solid which was further purified on another preparative TLC plate (250 µ, eluted with 75% acetone/methylene chloride three times) to give 0.050 g (56%) of the title compound as a yellow solid, mp 143°–144° C., along with 0.016 g (18%) of slightly less pure material.

$^1$H NMR (CDCl$_3$, 300MHz) δ: 7.60 (d, J=9.0 Hz, 2H), 7.58 (d, J=9.0 Hz, 2H), 7.21 (d, J=1.8 Hz, 1H), 7.08 (t, J=10.8 Hz, 1H), 6.93 (dd, J=10.8 Hz, J'=1.8 Hz 1H), 6.66 (d, J=9.9 Hz, 1H), 6.30 (bt, J=6.3 Hz, 1H), 4.80 (m, 10 lines, 1H), 4.11 (t, J=9.0 Hz, 1H), 3.90 (t, J=4.8 Hz, 4H), 3.84 (dd, J=9.3 Hz, J'=6.9 Hz, 1H), 3.70 (ddd, J=14.7 Hz, J'=6.0 Hz, J"=3.3 Hz, 1H), 3.64 (dt, J=14.7 Hz, J'=6.0 Hz, 1H), 3.37 (t, J=4.8 Hz, 4H), 2.03 (s, 3H).

$^{13}$C NMR (75.47MHz, CDCl$_3$): 0.01, 23.13, 41.98, 47.50, 49.09, 66.71, 72.01, 117.43, 118.26, 127.85, 128.59, 132.92, 134.45, 138.34, 147.58, 154.32, 159.57, 171.11, 181.55.

IR (mineral oil mull, cm$^{-1}$): 3307 (m), 1731 (s), 1658 (m), 1563 (s).

Mass Spectrum: m/e (rel. abundance): 423 (100,M$^+$), 424 (27.0), 380 (17.9), 379 (23.9), 364 (23.8), 280 (28.5), 152 (18.8), 86 (34.7), 56 (23.8), 29 calc'd for $C_{23}H_{25}N_3O_5$: 423.1794. Found: 423.1814.

Analysis calc'd for $C_{23}H_{25}N_3O_5$: C, 65.23; H, 5.95; N, 9.92. Found: C, 63.83; H, 5.90; N, 9.66.

TLC: 5% Methanol/Chloroform: $R_f$=0.29.

EXAMPLE 11

(S)-N-[[3-[4-(4-methoxy-5-oxo-1,3,6-cycloheptatrien-1-yl)-3,5-difluorophenyl]- 2-oxo-5-oxazolidinyl]methyl]acetamide.

The tris(dibenzylideneacetone)dipalladium(0)-chloroform adduct (450 mg, 0.492 mmol) and the trifurylphosphine (460 mg, 1.969 mmol) were stirred together for 5 min in 1,4-dioxane (25 mL), followed by the addition of (S)-N-[[3-(4-iodo- 3,5-difluorophenyl)-2-oxo-5-oxazolidinyl]methyl]acetamide (1.3 g, 3.28 mmol). After degassing the solution three times with $N_2$, the trimethyl(4-methoxy-5-oxo- 1,3,6-cycloheptatrien-1-yl)tin (1.47 g, 4.92 mmol) was added. The solution was degassed again (3×) and then the solution was heated to reflux (110 ° C.) for 12 h under $N_2$. Upon cooling, the reaction was determined to be complete by TLC (10% MeOH/CHCl$_3$, UV short wave). The reaction was concentrated under reduced pressure and then redissolved in CH$_2$Cl$_2$ (100 mL). This solution was stirred over aqueous KF (100 mL) for 45 min and then separated. The organic portion was washed with brine (100 mL) and then dried over anhydrous Na$_2$SO$_4$. After drying, it was filtered and concentrated under reduced pressure to yield a brown solid. The crude product was chromatographed on silica gel (175 g of silica gel, packed with 10% CH$_3$CN/CHCl$_3$, eluting with a gradient of 1–5% MeOH in 10% CH$_3$CN/CHCl$_3$) to give a pale yellow solid. This solid was recrystalized by dissolving it in CH$_2$Cl$_2$/MeOH and triturating with ether to yield 907 mg (68%) of the title compound as an off-white solid with mp 129 ° C (dec) and a HRMS (M$^+$) calculated for $C_{20}H_{18}N_2O_5F_2$ 404.1184, found 404.1183.

EXAMPLE 12

(±)-N-[[3-[4-(4-methoxy-5-oxo-1,3,6-cycloheptatrien-1-yl)- 3,5-difluorophenyl]-2-oxo-5-oxazolidinyl ]methyl ]acetamide.

The (±)-N-[[3-[4-(trimethylstannyl)-3,5-difluorophenyl ]-2-oxo- 5oxazolidinyl]methyl]acetamide (80 mg, 0.185 mmol) was dissolved in 1,4-dioxane ( 5 mL) and then treated with the 5-bromo-2-methoxytropolone (49.5 mg, .230 mmol). After degassing the solution 3 times with $N_2$, the bis(triphenylphosphine)palladium(II) chloride (28 mg, .040 mmol) was added. The solution was degassed (3x) again, after which the reaction was heated to reflux (110° C.) for 5 h. At this point, the reaction was incomplete; more catalyst (28 mg, 0.040 mmol) was added and, after degassing (3×), the solution was again heated to reflux for 5 h. At this time, the reaction was still incomplete; the above process was repeated a third time with more fresh catalyst (28 mg). Finally, the solvent was removed in vacuo and the residual oil was dissolved in CH$_2$Cl$_2$ (50 mL). The CH$_2$Cl$_2$ solution was washed with aqueous KF (75 mL) and brine (50 mL). After drying over anhydrous Na$_2$SO$_4$, the organic layer was filtered and concentrated under reduced pressure to yield a foamy solid. This solid was purified first by preparative TLC (5% MeOH/CHCl$_3$), and then by radial chromatography (eluting with a gradient of 0–5% MeOH in 10% CH$_3$CN/CHCl$_3$) to give 7 mg (9%) of the title compound as a solid with a HRMS (M$^+$) calculated for $C_{20}H_{18}F_2N_2O_5$ 404.1184, found 404.1183.

The (±)-N-[[3-(4-iodo-3,5-difluorophenyl)-2-oxo-5-oxazolidinyl]methyl ]acetamide (250 mg, 0.631 mmol) was dissolved in 1,4-dioxane (15 mL) and then treated with the stannyltropone (226 mg, 0.757 mmol). After degassing the solution 3 times with $N_2$, the bis(triphenylphosphine)palladium(II) chloride (70 mg, 0.10 mmol) was added. The solution was degassed again (3×) and then it was heated to reflux (110° C.) for 7 h. At this point, the reaction was incomplete; fresh catalyst (70 mg, 0.10 mmol) was added, and after degassing again (3×), the solution was again heated to reflux for 7 h. At this time, the solvent was removed in vacuo and the residual oil was dissolved in CH$_2$Cl$_2$ (50 mL). The CH$_2$Cl$_2$ solution was washed with aqueous KF (40 mL) and brine (40 mL). After drying over anhydrous Na$_2$SO$_4$, the organic layer was filtered and concentrated under reduced pressure to yield a foamy, brown solid. This solid was chromatographed on silica gel (100 g), eluting with a gradient of 0–10% MeOH in 10% CH$_3$CN/CHCl$_3$ to give impure product. This product was repurified by preparative TLC (5% MeOH/CHCl$_3$) to yield 72 mg (28%) of the title compound as an off-white solid with mp 218° C. (dec) and identical in all respects to material prepared as described above.

Key to the Name of the Compound 1. (±)-N[[3-[4-(4-methoxy-5-oxo-,1,3,6-cycloheptatrien-yl)phenyl]- 2-oxazolidinyl]methyl-acetamide,
2. (±)-N[[3-[4-(4-diethylamino-5-oxo-1,3,6-cycloheptatrien-1-yl)phenyl]- 2-oxo-5-oxazolidinyl]methyl]-acetamide
3. (±)-Acetamide, N-[[2-oxo-3-[4-[5-oxo-4-[(phenylmethyl)amino]- 1,3,6-cycloheptatrien-1-yl]phenyl]-5-oxazolidinyl]methyl]
4. (±)-N-[[3-[4-[4-[(2-hydroxyethyl)amino]-5-oxo1,3,6-cycloheptatrien- 1-yl]phenyl]-2oxo-5-oxazolidinyl]methyl-acetamide,
5. (±)-N-[[3-[4-[4-(4-morpholino)-5-oxo1,3,6-cycloheptatrien-1-yl]phenyl]2oxo5-oxazolidinyl]methyl]-acetamide,
6. (±)-N-[[3-[4-(4-cyclopropylamino-5-oxo-1,3,6-cycloheptatrien-1-yl)phenyl]- 2-oxo-5-oxazolidinyl]methyl]-acetamide,
7. (±)-N-[[3-[4-[4-(4-formyl-1-piperazinyl)-5-oxo-1,3,6-cycloheptatrien- 1-yl]phenyl]-2-oxo-5-oxazolidinyl]methyl]-acetamide,
8. (±)-N-[[3-[4-[4-(2-propenylamino)5-oxo-1,3,6-cycloheptatrien-1-yl]phenyl]-2-oxo-5-oxazolidinyl]methyl]-acetamide,
9. (±)-N-[[3-[4-[4-(1-pyrrolidinyl)-5-oxo-1,3,6-cycloheptatrien-1-yl]]phenyl]-2-oxo-5-oxazolidinyl]methyl]-acetamide,
10. (±)-N-[[3-[4-[4-(4-methyl-1-piperazinyl)-5-oxo-1,3,6-cycloheptatrien-1-yl]phenyl]-2-oxo-5-oxazolidinyl]methyl]-acetamide, 2-oxo-5-oxazolidinyl]methyl]-acetamide,
11. (±)-N-[[3-[4-(4-cyclopentylamino-5-oxo-1,3,6-cycloheptatrien-1-yl)phenyl]-2-oxo-5-oxazolidinyl]methyl]-acetamide,
12. (±)-N-[[3-[4-[4-(1-piperazinyl)-5-oxo-1,3,6-cycloheptatrien-1-yl]phenyl]-2-oxo-5-oxazolidinyl]methyl]-acetamide,
13.(±)-N-[[3-[4-(4-butylamino-5-oxo-1,3,6-cycloheptatrien-1-yl)phenyl]-2-oxo- 5-oxazolidinyl]methyl]-acetamide,
14. (±)-N-[[3-[4-[4-(cis-3,5-dimethyl-1-piperazinyl)-5-oxo-1,3,6-cycloheptatrien-1-yl]phenyl]-2-oxo5-oxazolidinyl] methyl]-acetamide,
15. (±)-N-[[3-[4-[4-(1-piperidinyl)-5-oxo-1,3,6-cycloheptatrien-1-yl]phenyl]-2-oxo-5-oxazolidinyl]methyl]-acetamide,
16. (±)-N-[[3-[3-fluoro-4-(4-methoxy-5-oxo-1,3,6-cycloheptatrien- 1-yl)phenyl]-2-oxo-5-oxazolidinyl]methyl]-acetamide,
17. (±)-N-[[3-[4-[4-(3-methyl-1-piperazinyl)-5-oxo-1,3,6-cycloheptatrien- 1-yl]phenyl]2-oxo-5-oxazolidinyl]methyl]-acetamide,
18. (±)-N-[[3-[4-[4-(3-hydroxy-1-pyrrolidinyl)-5-oxo-1,3,6-cycloheptatrien-1-yl]phenyl]-2-oxo-5oxazolidinyl]methyl]-acetamide, 19. (S)-N-[[3-fluoro-4-(4-methoxy-5-oxo-1,3,6-cycloheptatrien-1-yl]phenyl]-2-oxo-5-oxazolidinyl]methyl]-acetamide
20. (±)-N-[[3-[4-[4-methoxy-3-oxo-1,4,6-cycloheptatrien-1-yl)phenyl]-2-oxo- 5-oxazolidinyl]methyl]-acetamide,
21. (±)-N-[[3-[4-(6-methoxy-5-oxo-1,3,6-cycloheptatrien-1-yl]phenyl]-2-oxo5-oxazolidinyl]methyl]-acetamide,
22. (±)-N-[[3-[4-(4-ethoxy-5-oxo-1,3,6-cycloheptatrien-1-yl]phenyl]-2-oxo5-oxazolidinyl]methyl]-acetamide,
23. (±)-N-[[3-[4-[4-(3-amino- 1-yl)phenyl]-2-oxo-5-oxazolidinyl]methyl]-acetamide,
24. (±)-N[[3-[4-[4-(1-methylethoxy)-5-oxo-1,3,6-cycloheptatrien-1-yl]phenyl]-2-oxo-5-oxazolidinyl]methyl]-acetamide,
25. (S)-N-[[3-[4[4-(4-morpholino)-5-oxo-1,3,6-cycloheptatrien-1-yl]phenyl]-2-oxo-5-oxazolidinyl]methyl]-acetamide,
26. (±)-N[[3-[4-[4-(2-propenylamino)-3-oxo1,4,6-cycloheptatrien-1-yl]phenyl-2oxo-5-oxazolidinyl]methyl]-acetamide,
27. (±)-N-[]3-[4-4-(4-morpholinyl)-3-oxo-1,4,6-cycloheptatrien-1-yl]phenyl]-2-oxo-5-oxazolidinyl]methyl]-acetamide, and
28. (S)-N-[[3-[4-methoxy-5-oxo-1,3,6-cycloheptatrien-yl)phenyl-2-oxo- 5-oxazolidinyl)methyl]-acetamide,
29. (±)-N-[[3-[4-[4-(2-pyopynylamino)-3-oxo-1,4,6-cycloheptatrien- 1-yl)phenyl]2-oxo-5-oxazolidinyl]methyl-acetamide.
30. (±)-N-[[3-[4-[-[[(methoxycarbonyl)methyl]amino]-5-oxo-1,3,6cycloheptatrien-1-yl]phenyl]-2-oxo-5-oxazolidinyl]methyl]-acetamide,
31. (±)-N-[[3-[4-(4-methylamino--5-oxo1,3,6-cyclopheptatrien1-yl)phenyl]2-oxo-5-oxazolidinyl]methyl]-acetamide,
32. (±)-N-[[3-[4-[4-(2,5dihydro-1H--pyrrol-1-yl)-5-oxo-1,3,6-cycloheptatrien-1-yl]phenyl]-2-oxo-5-oxazolidinyl]methyl]-acetamide,
33. (±)-N-[[3-[4-[4-(2-propenyloxy)5-oxo-1,3,6-cycloheptatrien-1-yl]phenyl]-2-oxo-5-oxazolidinyl)methyl]-acetamide,
34. (S)-N-[[3-[3-fluoro-4-[(2propynlamino)5-oxo-1,3,6-cycloheptatrien- 1-yl)phenyl]-2-oxo-5oxazolidinyl]methyl-acetamide,
35. (±)-N-[[3-[4-[4-(2-methoxyethoxy)-5-oxo-1,3,6cycloheptatrien1-yl]phenyl)-2-oxo-5-oxazolidinyl]methyl]-acetamide,
36. (S)-N-[[3-[3-fluoro4[(4-morpholino)-5-oxo-1,3,6cycloheptatrien-1-yl]phenyl]-2-oxo-5oxazolidinyl]methyl]-acetamide,

TABLE 1

| Compound Number | Minimum Inhibitory Concentration in µg/ml in vitro | |
| --- | --- | --- |
| | Staphylococcus aureus UC® 9213 | Streptococcus pyogenes UC® 152 |
| Compound 1 | 2 | 0.25 |
| Compound 2 | 4 | 1 |
| Compound 3 | >64 | 4 |
| Compound 4 | 4 | 0.5 |
| Compound 5 | 2 | 0.5 |
| Compound 6 | 2 | 0.5 |
| Compound 7 | 4 | 0.5 |
| Compound 8 | 2 | 0.5 |
| Compound 9 | 4 | 1 |
| Compound 10 | 2 | 0.12 |
| Compound 11 | 4 | 1 |
| Compound 12 | 8 | 0.25 |
| Compound 13 | 2 | 0.5 |
| Compound 14 | 8 | 0.5 |
| Compound 15 | 2 | 1 |
| Compound 16 | 1 | 0.25 |
| Compound 17 | 8 | 0.25 |
| Compound 18 | 4 | 1 |
| Compound 19 | 1 | 0.25 |
| Compound 20 | 4 | 0.5 |
| Compound 21 | 64 | 8 |
| Compound 22 | 4 | 0.5 |
| Compound 23 | 16 | 0.25 |
| Compound 24 | 4 | 1 |
| Compound 25 | 2 | 0.5 |
| Compound 26 | 2 | 1 |
| Compound 27 | 4 | 1 |
| Compound 28 | 1 | |
| Compound 29 | 2 | 0.5 |
| Compound 30 | 4 | 1 |
| Compound 31 | 2 | 0.25 |
| Compound 32 | 32 | 4 |
| Compound 33 | 4 | 1 |
| Compound 34 | 1 | 0.25 |
| Compound 35 | 4 | 1 |
| Compound 36 | 2 | 0.5 |

I claim:

1. A compound having the Formula

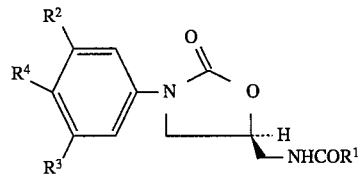

wherein $R^1$ is (a) Hydrogen (b) ($C_1$–$C_8$) alkyl optionally substituted with one or more of the following: F, Cl, hydroxy, alkoxy, acyloxy;

(c) ($C_3$–$C_6$) cycloalkyl (d) amino, (e) ($C_1$–$C_8$) alkylamino, (f) ($C_1$–$C_8$) dialkylamino, (g) ($C_1$–$C_8$) alkoxy wherein $R^2$ and $R^3$ are the same or different and are selected from the group consisting of:

(a) hydrogen (b) fluoro (c) chloro (d) ($C_1$–$C_8$) alkyl (e) trifluoromethyl (f) hydroxy (g) ($C_1$–$C_8$) alkoxy (h) nitro (i) amino with the proviso that when $R^2$ and $R^3$ are both other than hydrogen, then $R^2$ and $R^3$ are the same;

wherein $R^4$ is selected from the group consisting of

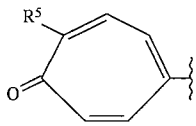 (a)

(b)

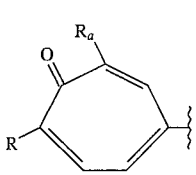 (c)

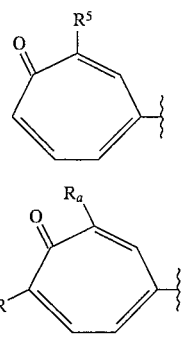 (d)

wherein R and $R_a$ are the same or different and are selected from the group consisting of $(C_1-C_8)$ alkyl optionally substituted with chloro, flouro, hydroxy, $(C_1-C_8)$ alkoxy, amino, $(C_1-C_8)$ alkylamino, $(C_1-C_8)$ dialkylamino;

wherein $R^5$ is selected from the group consisting of hydrogen, $OR^6$, $SR^6$, $NHR^7$,

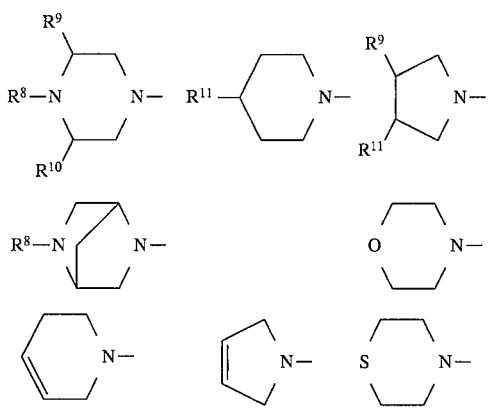

and $NR^7R^{12}$;

wherein $R^6$ is (a) hydrogen (b) $(C_1-C_8)$ alkyl optionally substituted with one or more halogens (c) $(C_1-C_8)$ alkyl optionally substituted with amino, $(C_1-C_8)$ alkylamino, $(C_1-C_8)$ dialkylamino (d) $(C_1-C_8)$ alkyl optionally substituted with one or more hydroxyls and with amino, alkylamino, dialkylamino (e) $(C_1-C_8)$ alkyl optionally substituted with one or more $(C_1-C_8)$ alkoxyls (f) $(C_2-C_8)$ alkenyl $(C_1-C_8)$ alkyl optionally substituted with amino, $(C_1-C_8)$ alkylamino, $(C_1-C_8)$ dialkylamino (g) $(C_2-C_8)$ alkynyl $(C_1-C_8)$ alkyl optionally substituted with amino, $(C_1-C_4)$ alkylamino, $(C_11-C_8)$ dialkylamino (h) $(C_2-C_8)$ acyl optionally substituted with hydroxyl, amino, $(C_1-C_8)$ alkylamino, $(C_1-C_4)$ dialkylamino (i) phenyl $(C_1-C_8)$ alkyl optionally substituted on phenyl with amino, $(C_1-C_8)$ alkylamino, $(C_1-C_8)$ dialkylamino (j) pyridyl $(C_1-C_8)$ alkyl optionally substituted on pyridyl with amino, $(C_1-C_8)$ alkylamino, $(C_1-C_8)$ dialkylamino (k) amino optionally substituted with one or two $(C_1-C_6)$ alkyl wherein $R^7$ is (a) hydrogen (b) $(C_1-C_8)$ alkyl optionally substituted by one or more chloro, flouro, hydroxy, amino $(C_1-C_8)$ alkylamino, $(C_1-C_8)$ dialkylamino, phenyl, pyridyl, $(C_1-C_8)$ alkoxyl, $(C_1-C_8)$ alkoxycarbonyl moieties, (c) $(C_3-C_8)$ cycloalkyl optionally substituted with amino, $(C_1-C_8)$ alkylamino or $(C_1-C_8)$ dialkylamino (d) amino, (e) $(C_1-C_8)$ alkylamino (f) $(C_1-C_8)$ dialkylamino (g) hydroxyl (h) $(C_1-C_8)$ alkoxyl (i) $(C_2-C_8)$ alkenyl $(C_1-C_{10})$ alkyl optionally substituted with amino, $(C_1-C_4)$ alkylamino, $(C_1-C_4)$ dialkylamino (j) $(C_2-C_8)$ alkynyl $(C_1-C_{10})$ alkyl optionally substituted with amino, $(C_1-C_4)$ alkylamino, $(C_1-C_4)$ dialkylamino wherein $R^8$ is (a) hydrogen (b) $(C_1-C_8)$ alkyl (c) $(C_3-C_8)$ cycloalkyl (d) $(C_1-C_8)$ acyl (e) $(C_1-C_8)$ alkoxycarbonyl (f) $(C_1-C_8)$ alkylsulfonyl wherein $R^9$ and $R^{10}$ maybe the same or different and are (a) hydrogen (b) $(C_1-C_8)$ alkyl wherein $R^{11}$ is (a) hydrogen (b) hydroxy (c) $(C_1-C_8)$ alkoxy (d) amino (e) alkylamino (f) $(C_1-C_8)$ dialkylamino (g) $(C_1-C_8)$ alkyl optionally substituted with amino $(C_1-C_4)$ alkylamino and $(C_1-C_4)$ dialkylamino;

wherein $R^{12}$ is $(C_1-C_8)$ alkyl;

or pharmaceutically acceptable salts and hydrates thereof.

2. A compound of claim 1 wherein $R^4$ is selection (a).

3. A compound of claim 2 which is (±)-N-[[3-[4-(4-methoxy-5-oxo-1,3,6-cycloheptatrien-yl)phenyl]-2-oxazolidinyl]methyl-acetamide, (±)-N-[[3-[4-(4-diethylamino-5-oxo-1,3,6-cycloheptatrien-1-yl)phenyl]-2-oxo- 5-oxazolidinyl]methyl]-acetamide (±)-N-[[2-oxo-3-[4[5-oxo-4-[(phenylmethyl)amino]-1,3,6-cycloheptatrien- 1-yl)phenyl]-5-oxazolidinyl]methyl-acetamide (±)-N-[[3-[4-[4-[(2-hydroxyethyl)amino]-5-oxo-1,3,6-cycloheptatrien- 1-yl]phenyl]-2-oxo-5-oxazolidinyl]methyl-acetamide, (±)-N-[[3-[4-[4-(4-morpholino)-5-oxo-1,3,6-cycloheptatrien-1-yl]phenyl]- 2-oxo-5-oxazolidinyl]methyl]-acetamide, (±)-N-[[3-[4-[4-(4-cyclopropylamino-5-oxo-1,3,6-cycloheptatrien-1-yl)phenyl-]2-oxo-5-oxazolidinyl]-methyl]-acetamide, (±)-N-[[3-[4-[4-(4-formyl-1-piperazinyl)-5-oxo-1,3,6-cycloheptatrien-1-yl]phenyl]-2-oxo-5-oxazolidinyl]methyl] -acetamide, (±)-N-[[3-[4-[4-(2-propenylamino)-5-oxo-1,3,6-cycloheptatrien-1-yl]phenyl]-2-oxo-5-oxazolidinyl]methyl]-acetamide, (±)-N-[[3-[4-4-(1-pyrrolidinyl)-5-oxo-1,3,6-cycloheptatrien-1-yl]]phenyl]-2-oxo-5-oxazolidinyl]methyl]-acetamide, (±)-N-[[3-[4-[4-(4-methyl-1-piperazinyl)-5oxo-1,3,6-cycloheptatrien-1-yl]phenyl]-2oxo-5oxazolidinyl]methyl]-acetamide, (±)-N-[[3-[4-(4-cyclopentylamino-5-oxo-1,3,6-cycloheptatrien-1-yl) phenyl]-2-oxo-5-oxazolidinyl]methyl]-acetamide, (±)-N-[[3-[4-[4-(1-piperazinyl)-5-oxo-1,3,6-cycloheptatrien-1-yl]phenyl]-2-oxo-5-oxazolidinyl]methyl]-acetamide, (±)-N-[[3-[4-[4-(4-butylamino-5-oxo-1,3,6-cycloheptatrien-1-yl) phenyl]-2-oxo-5-oxazolidinyl]methyl]-acetamide, (±)-N-[[3-[4-[4-(cis-3,5-dimethyl-1-piperazinyl)- 5-oxo-1,3,6-cycloheptatrien-1-yl]phenyl]-2-oxo-5-oxazolidinyl]methyl]-acetamide, (±)-N-[[3-[4-[4-(1-piperazinyl)-5-oxo-1,3,6-cycloheptatrien-1-yl]phenyl]-2-oxo-5-oxazolidinyl]methyl]-acetamide, (±)-N-[[3-[3-fluoro-4-(4-methoxy-5-oxo-1,3,6-cycloheptatrien-1yl)phenyl]- 2-oxo-5-oxazolidinyl]methyl]-acetamide, (±) -N-[[3-[4-[4-(3-methyl-1-piperadinyl)-5-oxo- 1,3,6-cycloheptatrien-1-yl]phenyl]-2-oxo-5-oxazolidnyl]methyl]-acetamide (±)-N-[[3-[4-[4-(3-hydroxy-1-pyrrolidinyl)-5-oxo- 1,3,6-cycloheptatrien-1-yl) phenyl]-2-oxo-5-oxazolidinyl]methyl]-acetamide, (S)-N-[[3-fluoro-4-(4-methoxy-5-oxo-1,3,6-cycloheptatrien- 1-yl)phenyl]-2-oxo-5-oxazolidinyl]methyl]-acetamide (±)-N-[[3-[4-[4-(4-ethoxy-5-oxo-1,3,6-cycloheptatrien-1-yl)phenyl]-2-oxo-5-oxazolidinyl]methyl]-acetamide, (±)-N-[[3-[4-[4-(3-amino-1-pyrrolidinyl)-5-oxo-1,3,6-cycloheptatrien-1-yl]phenyl]-2-oxo-5-oxazolidinyl]methyl] -acetamide, (±)-N-[[3-[4-[4-(1-methylethoxy)-5-oxo-1,3,6-cycloheptatrien-1-yl]phenyl]-2-oxo-5-oxazolidinyl]methyl]-acetamide, (S)-N-[[3-[4[4-(4-morpholino)-5-oxo-1,3,6-cycloheptatrien-1-yl]phenyl]-2-oxo-5-oxazolidinyl]methyl]-acetamide, (S)-N-[[3-[4-mexthoxy-5-oxo-1,3,6-cycloheptatrien-yl)phenyl- 2-oxo-5-oxazolidinyl)methyl]-acetamide, (±)-N-[[3-[4-(4-propoxy-5-oxo-1,3,6-cycloheptatrien-1-yl] phenyl]-2-oxo-5-oxazolidinyl]methyl]-acetamide, (±)-N-[[3-[4-[-[[(methoxycarbonyl)methyl]amino]-5-oxo-1, 3,6-cycloheptatrien-1-yl]phenyl]-2-oxo-5-oxazolidinyl] methyl]-acetamide, (±)-N-[[3-[4-(4-methylamino-5-oxo-1,3,6-cycloheptatrien-1-yl)phenyl]- 2-oxo-5-oxazolidinyl]methyl-acetamide, (±)-N-[[3-[4-[4-(2,5-dihydro-1H-pyrrol-1-yl)-5-oxo-1,3,6-cycloheptatrien- 1-yl]phenyl]-2-oxo-5-oxazolidinyl]methyl]-acetamide, (±)-N-[[3-[4-[4-(2-propenyloxy)-5-oxo-1,3,6-cycloheptatrien-1-yl]phenyl]-2-oxo-5-oxazolidinyl)methyl]-acetamide, (S)-N-[[3-[3-fluoro-4-[(2-propynlamino)5-oxo-1,3,6-cycloheptatrien-1-yl)phenyl]- 2-oxo-5-oxazolidinyl)methyl]-acetamide, (±)-N-[[3-[4-[4-(3,6-dihydro-1(2H)-pyridinyl)-5-oxo- 1,3, 6-cycloheptatrien-1-yl]-2-oxo-5-oxazolidinyl]methyl-acetamide, (I)-N-[[3-[4-[4-(2-methoxyethoxy)-5-oxo-1,3,6-cycloheptatrien-1-yl]phenyl)-2-oxo-5-oxazolidinyl]methyl]-acetamide, (S)-N-[[3-[3-fluoro-4-(4-morpholino)-5-oxo-1,3,6-cycloheptatrien-1-yl]phenyl]-2-oxo-5-oxazolidinyl]methyl]-acetamide, (±)-N-[[3-[3,5-difluoro-4-(4-methoxy-5-oxo-1,3,6-cycloheptatrien-1-yl)]-2-oxo-5-oxazolidinyl]methyl]-acetamide, (S)-N-[[3-[4-(4-methylamine-5-oxo-1,3,6-cycloheptatrien-1-yl)phenyl]- 2-oxo-5-oxazolidinyl]methyl)-acetamide, (S)-N-[[3-fluoro-4-(4-methylamino-5-oxo-1,3,6-cycloheptatrien-1-yl)Phenyl]- 2-oxo-5-oxazolidinyl]methyl]-acetamide, (S)-N-[[3-(4-(4-cyclopropyl)amino-5-oxo-1,3,6-cycloheptatrien-1-yl3-flouorphenyl]-2-oxo-5-oxazolidinyl)methyl]-acetamide, (S)-N-[[3-[4-[4-[(2-hydroxethyl)amino]-5-oxo-1,3,6-cycloheptatrien-1-yl]-phenyl]-2-oxo-5-oxazolidinyl)methyl]-acetamide, or (S)-N-[[2-oxo3-[3-fluor-4-[5-oxo-4-(phenylmethoxy)-1,3, 6-cycloheptatrien-1-yl]phenyl]-5-oxazolidinyl]methyl-acetamide.

4. A compound of claim 2 wherein $R_2$ and $R_3$ are independently hydrogen or flouro.

5. A compound of claim 4 which is (±)-N-[[3-[3-fluoro-4-(4-methoxy-5-oxo-1,3,6-cycloheptatrien-1-yl)phenyl]- 2-oxo-5-oxazolidinyl]methyl]-acetamide, (S)-N-[[3-[3-fluoro-4-(4-methoxy-5-oxo-1,3,6-cycloheptatrien-1-yl)phenyl]- 2-oxo-5-oxazolidinyl]methyl]-acetamide, (S)-N-[[3-[3-fluoro-4-[(2-propynlamino)-5-oxo-1,3,6-cycloheptatrien-1-yl)[phenyl]- 2-oxo-5-oxazolidinyl]methyl]-acetamide, (S)-N-[[3-[3-fluoro-4-[(4-morpholino)-5-oxo-1,3,6-cycloheptatrien-1-yl)]phenyl]- 2-oxo-5-oxazolidinyl]methyl]-acetamide, (±)-N-[[3-[3,5-difluoro-4-(4-methoxy-5-oxo-1,3,6-cycloheptatrien-1-yl)phenyl]- 2-oxo-5-oxazolidinyl]methyl]-acetamide, (S)-N-[[3-fluoro-4-(4-methylamino-5-oxo-1,3,6-cycloheptatrien-1-yl)Phenyl]- 2-oxo-5-oxazolidinyl]methyl-acetamide, (S)-N-[[2-oxo-3-(3-fluor-4-[5-oxo-4-(phenylmethoxy)-1,3, 6-cycloheptatrien- 1-yl]phenyl]-5-oxazolidinyl]methyl-acetamide, (S)-N-[[3-[4-(4-methoxy-5-oxo-1,3,6-cycloheptatrien-1-yl)-3,5-difluorophenyl]- 2-oxo-5-oxazolidinyl]methyl]-acetamide, or (±)-N-[[3-[4-(4-methoxy-5-oxo-1,3,6-cycloheptatrien-1-yl)-3,5-difluorophenyl]- 2-oxo-5-oxazolidinyl]methyl]-acetamide.

6. A compound of claim 1 wherein $R^4$ is selection (b).

7. A compound of claim 6 which is (±)-N-[[3-[4-[4-methoxy-3-oxo-1,4,6-cycloheptatrien-1-yl)phenyl]-2-oxo- 5-oxazolidinyl]methyl]-acetamide, (±)-N-[[3-[4-[-(2-propenyl)amino-3-oxo-1,4,6-cycloheptatrien-1-yl]phenyl]- 2-oxo-5-oxo-5-oxazolidinyl]methyl]-acetamide, (±)-N-[[3-[4-4-(4-morpholinyl)-3-oxo-1,4,6-cycloheptatrien-1-yl]phenyl]- 2-oxo-5-oxazolidinyl]methyl]-acetamide, or (±)-N-[[3-[4-[4-(2-propynylamino)-3-oxo-1,4,6-cyclohep tatrien-1-yl)phenyl]- 2-oxo-5-oxazolidinyl]methyl-acetamide.

8. A compound of claim 1 wherein $R^4$ is selection (c).

9. A compound of claim 8 which is (±)-N-[[3-[4-(6-methoxy-5-oxo-1,3,6-cycloheptatrien-1-yl)phenyl]-2-oxo- 5-oxazolidinyl]methyl]-acetamide.

10. A compound of claim 1 wherein $R^4$ is selection (d).

* * * * *

UNITED STATES PATENT AND TRADEMARK OFFICE
CERTIFICATE OF CORRECTION

PATENT NO. : 5,523,403
DATED : June 4, 1996
INVENTOR(S) : Michael R. Barbachyn

It is certified that error appears in the above-identified patent and that said Letters Patent is hereby corrected as shown below:

Cover Page, Column 2, line 15, "Carson, Randall K." should read -- Carlson, Randall K. --. Column 6, line 15, "rioufo" should read -- fluoro --. Column 20, in Chart 7, lines 35-45, the seven-member ring of the structure labeled Ia (racemic) should appear as follows

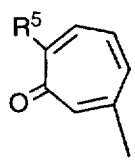

Column 20, line 53, "Iodoeyeloeaarbamation" should read -- Iodocyclocarbamation --. Column 20, line 59, "ratemit" should read -- racemic --. Column 20, line 60, "raeemie" should read -- racemic --. Column 21, line 3-4, 3 occurrences of "sulfonie" should read -- sulfonic --. Column 21, line 4, "earboxylic" should read -- carboxylic --. Column 21, lines 45-46, "*M. aviurn*" should read -- *M. avium* --. Column 22, line 6, "MS (E1):" should read -- MS (EI): --. Column 23, line 1, "$R_s$ product" should read -- $R_f$ product --. Column 23, line 63, "solidired" should read -- solidified --. Column 24, line 13, "refiuxing" should read -- refluxing --. Column 24, line 34, " N, " should read -- N, 4.88 --. Column 24, lines 64-65, "(trifi-uoromethyl)" should read -- (trifluoromethyl) --. Column 24, line 67, "$\geq$" should read -- $\geq$ --. Column 27, line 18, "J'4.5 Hz," should read -- J' = 4.5 Hz, --. Coumn 27, line 34, "before th" should read -- before the --. Column 27, line 44, "0-3% McOH" should read -- 0-3% MeOH --. Column 27, line 44, "CH$_3$CH/" should read -- CH$_3$CN/ --. Column 27, line 48, "-2-oxo5-oxazo" should read -- -2-oxo-5-oxazo --. Column 27, line 49, "-toluensulfonate." should read -- toluenesulfonate. --. Column 27, line 51, "puridine" should read -- pyridine --. Column 27, line 54, "in the cole" should read --

UNITED STATES PATENT AND TRADEMARK OFFICE
CERTIFICATE OF CORRECTION

PATENT NO. : 5,523,403
DATED : June 4, 1996
INVENTOR(S) : Michael R. Barbachyn

Page 2 of 3

It is certified that error appears in the above-identified patent and that said Letters Patent is hereby corrected as shown below:

in the cold --. Column 27, line 55, "the produce" should read -- the product --. Column 27, line 58, "unde high" should read -- under high --. Column 27, line 61, "($M^{30}$)" should read -- ($M^+$) --. Column 27, lines 63-64, "2-oxo5-ox-azolindinyl]" should read -- 2-oxo-5-oxazolidinyl] --. Column 27, line 65, "2-oxo5-oxazolindinyl]" should read -- 2-oxo-5-oxazolidinyl] --. Column 28, line 15, "254,0609." should read -- 254.0609. --. Column 28, line 16 "Presparation" should read -- Preparation --. Column 28, line 18, "2-oxo5-oxazolindinyl]" should read -- 2-oxo-5-oxazolidinyl]". Column 28, line 27, "After and" should read -- After an --. Column 28, line 45, "wash with" should read -- washed with --. Column 28, line 45, "$MaHCO_3$" should read -- $NaHCO_3$ --. Column 29, line 5, "N-carbobenzyloxyo3,5-" should read --N-carbobenzyloxy-3,5- --. Column 30, line 45, "with $IC_1$" should read -- with ICI --. Column 30, line 49, "a glass flit. " should read -- a glass frit. --. Column 31, line 22, "tatrien- ly)phenyl]" should read -- tatrien-1-yl)phenyl] --. Column 31, line 34, "$CH_2C_{12}$" should read -- $CH_2CL_2$ --. Column 31, line 46, "J+9.2 Hx)," should read -- J+9.2 Hz), --. Column 31, line 52, "tatrien- 1-yl))" should read -- tatrien-1-yl) --. Column 32, line 4, "$CH_2C_{12}$" should read -- $CH_2CL_2$ --. Column 32, line 9, "and top." should read -- and mp. --. Column 32, line 33, "hu 1H NMR" should read -- $^1$H NMR --. Column 32, line 34, "682" should read -- 6.82 --. Column 33, line 2, "-2yl]" should read -- -2-yl] --. Column 33, line 25, "J=0.7" should read -- J=10.7 --. Column 34, line 23, "J=112 Hz)" should read -- J=11.2 Hz) --. Column 34, line 47, "100 (t," should read -- 1.00 (t, --. Column 35, lines 17-18, "hydroxypyrrolidin-1-yl- " should read -- hydroxypyrrolidin-1-yl)--. Column 37, line 15, "-±-N" should read -- ±-N --. Column 37, line 58, "1yl]phjenyl]" should read -- 1-yl]phenyl] --. Column 38, line 21, "$C_{22}H$" should read -- $C_{22}H_{23}N_3O_4$ --. Column 38, line 29, "1yl]phenyl]"

UNITED STATES PATENT AND TRADEMARK OFFICE
CERTIFICATE OF CORRECTION

PATENT NO. : 5,523,403
DATED : June 4, 1996
INVENTOR(S) : Michael R. Barbachyn

It is certified that error appears in the above-identified patent and that said Letters Patent is hereby corrected as shown below:

should read -- 1-yl]phenyl] --. Column 38, line 58, "29 calc'd for" should read -- 29 (23.3); exact mass calc'd for --. Column 39, line 34, "5oxazolidinyl]" should read -- 5-oxazolidinyl] --. Column 40, Item 4 at line 23, "2oxo-5-" should read -- 2-oxo-5- --. Column 40, Item 5 at line 25, "5-oxo1,3,6" should read -- 5-oxo-1,3,6 --. Column 40, Item 5 at line 26, "2oxo5-" should read -- 2-oxo-5- --. Column 40, Item 8 at line 34, ")5-oxo" should read -- )-5-oxo --. Column 40, Item 14 at line 54, "2-oxo5-" should read -- 2-oxo-5- --. Column 40, Item 18 at line 66, "oxo-5oxazolidinyl]" should read -- oxo-5-oxazolidinyl] --. Column 41, Item 21 at line 7, "oxo5-oxazolidinyl]" should read -- oxo-5-oxazolidinyl] --. Column 41, Item 22 at line 9, "2-oxo5-" should read -- 2-oxo-5- --. Column 41, Item 23 at line 10, "(3-amino-1-yl]" should read -- (3-amino-1-pyrrolidinyl)-5-oxo-1,3,6-cycloheptatrien-1-yl] --. Column 41, Item 26 at line 18, "oxo1,4,6-cyclo" should read -- oxo-1,4,6-cyclo --. Column 41, Item 26 at line 19, "2oxo-5-" should read -- 2-oxo-5- --. Column 41, Item 30 at line 30, "1,3,6cycloheptatrien" should read -- 1,3,6-cycloheptatrien --. Column 41, Item 31 at lines 32-33, "5-oxo1,3,6-cyclopheptatrien1-yl)" should read -- 5-oxo-1,3,6-cycloheptatrien-1-yl) --. Column 41, Item 32 at line 35, "(2,5dihydro-1H--pyrrol" should read -- (2,5-dihydro-1H-pyrrol --. Column 41, Item 32 at lines 36-37 "oxazolidinyl]methyl]" should read -- oxazolidinyl[methyl] --. Column 41, Item 33 at line 38, ")5-oxo" should read -- )-5-oxo --. Column 41, Item 34 at line 42, "5oxazolidinyl]" should read -- 5-oxazolidinyl] --. Column 41, Item 35 at lines 44-45, "1,3,6cycloheptatrien1-yl]" should read -- 1,3,6-cycloheptatrien-1-yl] --. Column 41, Item 36 at line 47, "1,3,6cyclo" should read -- 1,3,6-cyclo --. Column 41, Item 36 at line 48, "5oxazolidinyl]" should read -- 5-oxazolidinyl] --. Column 43, line 10, structure (b) should appear as

UNITED STATES PATENT AND TRADEMARK OFFICE
CERTIFICATE OF CORRECTION

PATENT NO. : 5,523,403
DATED : June 4, 1996
INVENTOR(S) : Michael R. Barbachyn

It is certified that error appears in the above-identified patent and that said Letters Patent is hereby corrected as shown below:

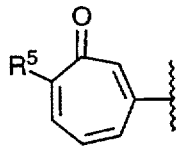

Column 45, line 19, "5oxo-1,3,6-" should read -- 5-oxo-1,3,6- --. Column 45, line 20, "2oxo-5oxazolidinyl]" should read -- 2-oxo-5-oxazolidinyl] --. Column 46, line 20, "1-yl)]-2-" should read -- 1-yl)phenyl]-2- --. Column 46, line 25, "methyl]-" should read -- methyl- --. Column 46, line 28, "yl3-flouorphenyl]" should read -- yl-3-fluorophenyl] --.

Signed and Sealed this

Sixth Day of April, 1999

Attest:

Q. TODD DICKINSON

*Attesting Officer*     *Acting Commissioner of Patents and Trademarks*